United States Patent [19]
Dombroski et al.

[11] Patent Number: 6,117,874
[45] Date of Patent: Sep. 12, 2000

[54] BENZOPYRAN AND BENZO-FUSED COMPOUNDS, THEIR PREPARATION AND THEIR USE AS LEUKOTRIENE B$_4$ (LTB$_4$) ANTAGONISTS

[75] Inventors: Mark Anthony Dombroski, Waterford, Conn.; Kevin Koch, Boulder; Anthony Daniel Piscopio, Longmont, both of Colo.

[73] Assignee: Pfizer Inc., New York, N.Y.

[21] Appl. No.: 09/241,209

[22] Filed: Feb. 1, 1999

Related U.S. Application Data

[63] Continuation of application No. 08/809,727, filed as application No. PCT/IB95/00397, May 26, 1995, Pat. No. 5,939,452, and a continuation of application No. 08/322,853, Oct. 13, 1994, abandoned.

[51] Int. Cl.$^7$ ...................... A61K 31/47; A61K 31/4709; C07D 215/233; C07D 401/04; C07D 401/06
[52] U.S. Cl. .................... 514/253.07; 514/269; 514/278; 514/311; 514/314; 514/307; 544/333; 544/405; 546/18; 546/145; 546/165
[58] Field of Search ..................................... 544/333, 405; 546/18, 148, 165; 514/252, 269, 278, 311, 314, 307, 253.07

[56] References Cited

U.S. PATENT DOCUMENTS

| | | | |
|---|---|---|---|
| 4,565,882 | 1/1986 | Miyano et al. | 549/399 |
| 4,996,230 | 2/1991 | Gapinski | 514/454 |
| 5,550,152 | 8/1996 | Koch et al. | 514/458 |
| 5,684,046 | 11/1997 | Koch | 514/569 |

FOREIGN PATENT DOCUMENTS

| | | |
|---|---|---|
| 0276064 | 7/1988 | European Pat. Off. |
| 0292977 | 11/1988 | European Pat. Off. |
| 0405116 | 1/1991 | European Pat. Off. |
| 2257282 | 8/1975 | France . |
| 9117160 | 11/1991 | WIPO . |
| 9117989 | 11/1991 | WIPO . |
| 9200011 | 1/1992 | WIPO . |
| 9315066 | 8/1993 | WIPO . |
| 9315067 | 8/1993 | WIPO . |

OTHER PUBLICATIONS

Djuric, S. W. et al., J. Med. Chem., 32(6), 1145–7, (1989).
Marder, P. et al., Prostaglandins Leukotrienes and Essential Fatty Acids (1992), 46, 265–270.
Pettipher, E. R. et al., Br. J. Pharmacol. (1993), 110, 423–427.
Harvath, L., J. Immunology, 139(9), 3055–3061, (1987).
Sherman, J. W., J. Immunology, 140 (11), 3900–3904, (1988).
Lichtenberger, J. et al., Bulletin De La Societe Chimique de France, 1963, pp. 275–282, No. 47.
Aono, T. et al., Chemical & Pharmaceutical Bulletin, vol. 26, No. 5, May 1978, pp. 1511–1521.
Panetta, C. A. et al., Synthesis, No. 1, Jan. 1981, pp. 59–60.
Serges, R. et al., J. Med. Chem., vol. 31, No. 1, Jan. 1988, pp. 230–243.
Horaguchi, T. et al., J. C. S., Chem. Comm., No. 1, Jan. 1991, pp. 44–46.
Duewell, H. et al., Australian J. of Chem., vol. 41, No. 4, 1988, pp. 535–548.
Bethune, R. J. et al., J. Chem. Soc., Perkin Transactions 1, No. 14, Jul. 1994, pp. 1925–1933.

*Primary Examiner*—Richard L. Raymond
*Attorney, Agent, or Firm*—P. C. Richardson; P. H. Ginsburg; J. W. Appleman

[57] ABSTRACT

This invention relates to novel benzopyran and other benzo-fused leukotriene B$_4$ (LTB$_4$) antagonists and the pharmaceutically acceptable salts thereof, to pharmaceutical compositions containing such compounds, and to a method of using such compounds as LTB$_4$ antagonists. The compounds of this invention inhibit the action of LTB$_4$ and are therefore useful in the treatment of LTB$_4$ induced illnesses such as inflammatory disorders including rheumatoid arthritis, osteoarthritis, inflammatory bowel disease, psoriasis and other skin disorders such as eczema, erythema, pruritus and acne, stroke and other forms of reperfusion injury, graft rejection, autoimmune diseases, asthma, and other conditions where marked neutrophil infiltration occurs.

12 Claims, No Drawings

BENZOPYRAN AND BENZO-FUSED COMPOUNDS, THEIR PREPARATION AND THEIR USE AS LEUKOTRIENE B₄ (LTB₄) ANTAGONISTS

CROSS REFERENCE TO RELATED APPLICATIONS

This application is a continuation of U.S. application Ser. No. 08/809,727 filed Apr. 9, 1997, now U.S. Pat. No. 5,939,452, which is a 371 of International Application No. PCT/IB95/00397 having an international filing date of May 26, 1995, designating inter alia, the United States which is a continuation of U.S. application Ser. No. 08/322,853, filed Oct. 13, 1994, now abandoned.

BACKGROUND OF THE INVENTION

This invention relates to novel benzopyran and other benzo-fused leukotriene $B_4$ ($LTB_4$) antagonists, the pharmaceutically acceptable salts of said compounds, to pharmaceutical compositions containing such compounds, and to a method of using such compounds as $LTB_4$ antagonists.

The compounds of this invention inhibit the action of $LTB_4$ and are therefore useful in the treatment of $LTB_4$ induced illnesses such as inflammatory disorders including rheumatoid arthritis, osteoarthritis, inflammatory bowel disease, psoriasis and other skin disorders such as eczema, erythema, pruritus and acne, stroke and other forms of reperfusion injury, graft rejection, autoimmune diseases, asthma, and other conditions where marked neutrophil infiltration occurs.

Leukotriene $B_4$ antagonists are disclosed in European patent publications 276 064 and 292 977 which refer to diphenylethers, benzophenones, and other compounds containing two phenyl groups, and 7-(3-alkoxy4-alkanoyl-phenoxy)alkoxy benzopyran derivatives, respectively.

SUMMARY OF THE INVENTION

The present invention is directed to novel benzopyran and other benzo-fused leukotriene $B_4$ ($LTB_4$) antagonist compounds, of the formula

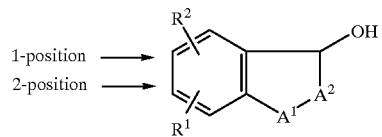

(I)

and the pharmaceutically acceptable salts thereof
wherein $A^1$ is O, $CH_2$, S, NH or $N(C_1-C_6)$alkyl;

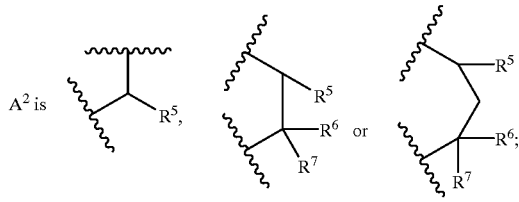

$R^5$ is selected from the group consisting of $-(CH_2)_n CHX^9X^{10}$, $-(CH_2)_nX^{10}$, $-O(CH_2)_qCHX^9X^{10}$, and $-O(CH_2)_qX^{10}$;
wherein n is 0, 1, 2, or 3;

q is 0, 1 or 2;
$X^9$ is hydrogen, $(C_1-C_6)$alkyl or optionally substituted phenyl;
wherein the optionally substituted phenyl is optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl and phenylsulfonyl;
$X^{10}$ is hydrogen, $(C_1-C_6)$alkyl, $(C_3-C_8)$cycloalkyl or one of the following optionally substituted rings: phenyl, thienyl, pyridyl, furyl, naphthyl, quinolyl, isoquinolyl, pyrimidinyl or pyrazinyl;
where the optionally substituted rings are optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, phenylsulfonyl and optionally substituted phenyl;
where the optionally substituted phenyl is optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl and phenylsulfonyl;
$R^6$ and $R^7$ are each independently hydrogen or $(C_1-C_4)$alkyl or $R^6$ and $R^7$ are taken together with the carbon atom to which they are attached and form $(C_4-C_7)$cycloalkyl;
$R^1$ is selected from the group consisting of tetrazolyl, carboxy, cis or trans $-(CH_2)_mCX^1=CX^2-CO_2H$, $-(CH_2)_mCX^3X^4X^5$, $-CO-NG^1G^2$,

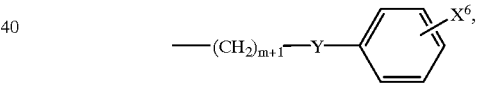

and a substituted five or six membered aromatic ring optionally having one or two heteroatoms where the heteroatoms are independently selected from the group consisting of O, S and N;
wherein m is 0, 1 or 2;
Y is O, $CH_2$, S, NH or $N(C_1-C_6)$alkyl;
$X^1$ and $X^2$ are each independently hydrogen or $(C_1-C_6)$alkyl;
$X^3$ and $X^4$ are each independently hydrogen or $(C_1-C_6)$alkyl, or $X^3$ and $X^4$ are taken together with the carbon atom to which they are attached and form $(C_3-C_7)$cycloalkyl;
$X^5$ is hydroxy, carboxy, tetrazolyl or $-CO-NG^3G^4$;
$X^6$ is carboxy, tetrazolyl, $CH_2OH$ or $-CO-NG^5G^6$;
$G^1$, $G^2$, $G^3$, $G^4$, $G^5$, and $G^6$ are each independently selected from the group consisting of hydrogen, $(C_1-C_ )$alkyl, $(C_1-C_4)$perfluoroalkyl, $(C_1-C_6)$alkylsulfinyl, phenylsulfinyl, $(C_1-C_6)$alkylsulfonyl, phenylsulfonyl, hydroxy, phenyl and $(Q^1)_a$-substituted phenyl;
where a is 1 or 2;
$Q^1$ for each occurrence is independently selected from the group consisting of fluoro, chloro, $(C_1-C_6)$-alkyl, $(C_1-C_)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkyl-sulfonyl and phenylsulfonyl;

the substituted five or six membered aromatic ring is substituted with one substituent selected from the group consisting of carboxy, tetrazolyl, —CO—N(H)(SO$_2$—X$^7$), —N(H)(SO$_2$—X$^7$), —N(H)(CO—X$^7$), and —N(H)(CO—OX$^7$) and with one or two substituents each independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, and phenylsulfonyl;

wherein X$^7$ is hydrogen, —CH$_2$F, —CHF$_2$, —CF$_3$, $(C_1-C_6)$alkyl, $(C_3-C_8)$cycloalkyl or one of the following optionally substituted rings: phenyl, thienyl, pyridyl, furyl, naphthyl, quinolyl, isoquinolyl, pyrimidinyl or pyrazinyl;

where the optionally substituted rings are optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, phenylsulfonyl and optionally substituted phenyl;

where the optionally substituted phenyl is optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfonyl, $(C_1-C_6)$alkylsulfonyl and phenylsulfonyl;

R$^2$ is hydrogen, fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl or phenylsulfonyl;

with the provisos that:

G$^1$ and G$^2$ are not hydroxy at the same time;

G$^3$ and G$^4$ are not hydroxy at the same time;

G$^5$ and G$^6$ are not hydroxy at the same time;

R$^1$ is not phenyl substituted with carboxy, tetrazolyl or —CO—NH—SO$_2$—X$^7$ when R$^1$ is in the 1-position or 2-position; and R$^1$ is not carboxy, cis or trans —(CH$_2$)$_m$—CX$^1$=CX$^2$—CO$_2$H, —(CH$_2$)$_m$CX$^3$X$^4$X$^5$ or

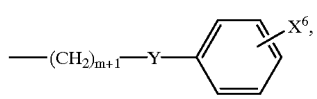

where X$^6$ is carboxy, tetrazolyl or CH$_2$OH, when R$^1$ is in the 1-position or 2-position.

A preferred group of compounds are those compounds of formula I or a pharmaceutically acceptable salt thereof wherein A$^2$ is

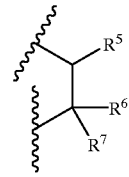

where R$^6$ and R$^7$ are each hydrogen; and R$^1$, R$^2$, A$^1$, and R$^5$ are as defined above for formula I.

A more preferred group of compounds are those compounds of formula I or a pharmaceutically acceptable salt thereof wherein A$^1$ is O or CH$_2$; A$^2$ is

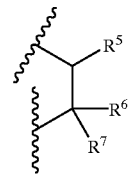

where R$^6$ and R$^7$ are each hydrogen; and R$^1$, R$^2$, and R$^5$ are as defined above for formula I.

A yet more preferred group of compounds are those compounds of formula I or a pharmaceutically acceptable salt thereof wherein A$^1$ is O or CH$_2$; A$^2$ is

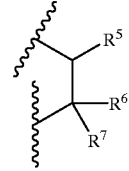

where R$^6$ and R$^7$ are each hydrogen; R$^1$ is —(CH$_2$)$_m$CX$^3$X$^4$X$^5$ or a substituted five or six membered aromatic ring substituted with one substituent selected from the group consisting of carboxy, tetrazolyl, —CO—N(H)(SO$_2$—X$^7$), —N(H)(SO$_2$—X$^7$), —N(H)(CO—X$^7$), and —N(H)(CO—OX$^7$) and with one or two substituents each independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_)$alkylthio, $(C_1-C_6)$alkylsulfinyl, phenylsulfinyl, $(C_1-C_6)$alkylsulfonyl, and phenylsulfonyl; and m, X$^3$, X$^4$, X$^5$, X$^7$, R$^2$, and R$^5$ are as defined above for formula I.

An even more preferred group of compounds are those compounds of formula I or a pharmaceutically acceptable salt thereof wherein A$^1$ is O or CH$_2$; A$^2$ is

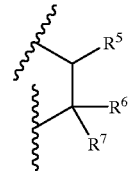

where R$^6$ and R$^7$ are each hydrogen; R$^1$ is a substituted phenyl substituted with one substituent selected from the group consisting of carboxy, —N(H)(SO$_2$—X$^7$), —N(H)(CO—X$^7$), and —N(H)(CO—OX$^7$) and with one or two substituents each independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, and phenylsulfonyl; and $X^7$, $R^2$, and $R^5$ are as defined above for formula I.

A most preferred group of compounds are those compounds of formula I or a pharmaceutically acceptable salt thereof wherein $A^1$ is O or $CH_2$; $A^2$ is

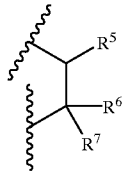

where $R^6$ and $R^7$ are each hydrogen; $R^1$ is a substituted phenyl substituted with one substituent selected from the group consisting of carboxy, and —N(H)(SO$_2$—$X^7$), and with one or two substituents each independently selected from the group consisting of fluoro, chloro, $(C_1-C_1)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, and phenylsulfonyl; and $X^7$, $R^2$ and $R^5$ are as defined above for formula I.

Another most preferred group of compounds are those compounds of formula I or a pharmaceutically acceptable salt thereof wherein $A^1$ is O or $CH_2$; $A^2$ is

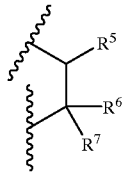

where $R^6$ and $R^7$ are each hydrogen; $R^1$ is a substituted phenyl substituted with one substituent selected from the group consisting of carboxy, and —N(H)(SO$_2$—$X^7$), and with one or two substituents each independently selected from the group consisting of fluoro, chloro, $(C_1-C_6)$alkyl, $(C_1-C_1)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, and phenylsulfonyl; $R^5$ is —(CH$_2$)$_n$CHX$^9$X$^{10}$ where $X^9$ is hydrogen and $X^{10}$ is one of the optionally substituted rings defined above for formula I; and $X^7$, and $R^2$ are as defined above for formula I. A preferred group of compounds within the immediately foregoing group of compounds are those compounds wherein n is 1; and $X^{10}$ is phenyl or phenyl substituted at the para position with phenyl. And the following group of compounds is the most preferred group of compounds hereof wherein $R^1$ is a substituted phenyl substituted with one substituent selected from the group consisting of carboxy and —N(H)(SO$_2$—$X^7$), and with one or two substituents each independently selected from the group consisting of fluoro, chloro and $(C_1-C_4)$perfluoroalkyl.

The present invention also relates to pharmaceutical compositions for the treatment of LTB$_4$ induced illnesses which comprise an effective amount of a compound of the formula I, as defined above, or a pharmaceutically acceptable salt thereof and a pharmaceutically acceptable carrier or diluent. The invention further relates to pharmaceutical compositions for the treatment of anti-inflammatory disorders, eczema, erythema, pruritus, acne, stroke, graft rejection, autoimmune diseases, and asthma which comprise an effective amount of a compound of the formula I, as defined above, or a pharmaceutically acceptable salt thereof and a pharmaceutically acceptable carrier or diluent.

This invention further comprises a method for the receptor binding inhibition, functional inhibition and in vivo inhibition of LTB$_4$ which comprises administering to a subject in need of such inhibition an effective amount of a compound of formula I, as defined above, or a pharmaceutically acceptable salt thereof. The invention includes methods for the treatment of inflammatory disorders, eczema, erythema, pruritus, acne, stroke, graft rejection, autoimmune diseases, and asthma which comprise administering to a subject in need of such treatment an effective amount of a compound of formula I, as defined above, or a pharmaceutically acceptable salt thereof.

The invention is also directed to intermediate compounds of the formula 1A

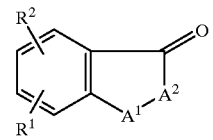

(1A)

wherein $A^1$ is O, $CH_2$, S, NH or N($C_1-C_6$)alkyl;

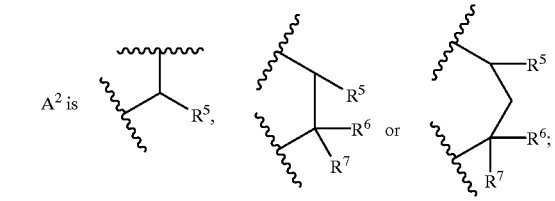

$A^2$ is $R^5$ is selected from the group consisting of —(CH$_2$)$_n$CHX$^9$X$^{10}$, —(CH$_2$)$_n$X$^{10}$, —O(CH$_2$)$_q$CHX$^9$X$^{10}$, and —O(CH$_2$)$_q$X$^{10}$;
wherein n is 0, 1, 2, or 3;
q is 0, 1 or 2;
$X^9$ is hydrogen, $(C_1-C_6)$alkyl or optionally substituted phenyl;
wherein the optionally substituted phenyl is optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl and phenylsulfonyl;
$X^{10}$ is hydrogen, $(C_1-C_6)$alkyl, $(C_3-C_8)$cycloalkyl or one of the following optionally substituted rings: phenyl, thienyl, pyridyl, furyl, naphthyl, quinolyl, isoquinolyl, pyrimidinyl or pyrazinyl;
where the optionally substituted rings are optionally substituted with fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_1)$alkylsulfinyl, phenylsulfinyl, $(C_1-C_6)$alkylsulfonyl, phenylsulfonyl and optionally substituted phenyl;
where the optionally substituted phenyl is optionally substituted with one or two substituents independently selected from the group consisting of fluoro, chloro, $(C_1-C_6)$alkyl, $(C_1-C_6)$ alkoxy, $(C_1-C_4)$perfluoroalkyl, $(C_1-C_4)$ perfluoroalkoxy, $(C_1-C_6)$alkylthio, $(C_1-C_6)$ alkylsulfinyl, phenylsulfinyl, $(C_1-C_6)$ alkylsulfonyl and phenylsulfonyl;

$R^6$ and $R^7$ are each independently hydrogen or $(C_1-C_4)$ alkyl, or $R^6$ and $R^7$ are taken together with the carbon atom to which they are attached and form $(C_4-C_7)$ cycloalkyl;

$R^1$ is selected from the group consisting of tetrazolyl, carboxy, cis or trans $-(CH_2)_m CX^1=CX^2-CO_2H$, $-(CH_2)_m CX^3X^4X^5$, $-CO-NG^1G^2$,

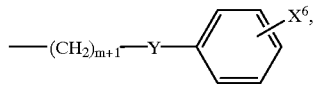

and a substituted 5 or 6 membered aromatic ring optionally having one or two heteroatoms where the heteroatoms are independently selected from the group consisting of O, S and N;

wherein m is 0, 1 or 2;

Y is O, $CH_2$, S, NH or $N(C_1-C_6)$alkyl;

$X^1$ and $X^2$ are each independently hydrogen or $(C_1-C_6)$ alkyl;

$X^3$ and $X^4$ are each independently hydrogen or $(C_1-C_6)$ alkyl, or $X^3$ and $X^4$ are taken together with the carbon atom to which they are attached and form $(C_3-C_7)$ cycloalkyl;

$X^5$ is hydroxy, carboxy, tetrazolyl or $-CO-NG^3G^4$;

$X^6$ is carboxy, tetrazolyl, $CH_2OH$ or $-CO-NG^5G^6$;

$G^1$, $G^2$, $G^3$, $G^4$, $G^5$, and $G^6$ are each independently selected from the group consisting of hydrogen, $(C_1-C_6)$alkyl, $(C_1-C_4)$perfluoroalkyl, $(C_1-C_6)$ alkylsulfinyl, phenylsulfinyl, $(C_1-C_6)$alkylsulfonyl, phenylsulfonyl, hydroxy, phenyl and $(Q^1)_a$-substituted phenyl;
where a is 1 or 2;
$Q^1$ for each occurrence is selected from fluoro, chloro, $(C_1-C_6)$-alkyl, $(C_1-C_6)$alkoxy, $(C_1-C_4)$ perfluoroalkyl, $(C_1-C_4)$perfluoroalkoxy, $(C_1-C_6)$ alkylthio, $(C_1-C_6)$alkylsulfinyl, phenylsulfinyl, $(C_1-C_6)$alkylsulfonyl and phenylsulfonyl;

the substituted five or six membered aromatic ring is substituted with one substituent selected from the group consisting of carboxy, tetrazolyl, $-CO-N(H)$ $(SO_2-X^7)$, $-N(H)(SO_2-X^7)$, $-N(H)(CO-X^7)$, and $-N(H)(CO-OX^7)$ and with one or two substituents each independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$alkylthio, $(C_1-C_6)$alkylsulfinyl, phenylsulfinyl, $(C_1-C_6)$alkylsulfonyl, and phenylsulfonyl;
wherein $X^7$ is hydrogen, $-CH_2F$, $-CHF_2$, $-CF_3$, $(C_1-C_6)$alkyl, $(C_3-C_8)$cycloalkyl or one of the following optionally substituted rings: phenyl, thienyl, pyridyl, furyl, naphthyl, quinolyl, isoquinolyl, pyrimidinyl or pyrazinyl;
where the optionally substituted rings are optionally substituted with one or two substituents independently selected from fluoro, chloro, $(C_1-C_6)$alkyl, $(C_1-C_6)$alkoxy, $(C_1-C_4)$perfluoroalkyl, $(C_1-C_4)$ perfluoroalkoxy, $(C_1-C_6)$alkylthio, $(C_1-C_6)$ alkylsulfinyl, phenylsulfinyl, $(C_1-C_6)$ alkylsulfonyl, phenylsulfonyl and optionally substituted phenyl;
where the optionally substituted phenyl is optionally substituted with one or two substituents independently selected from the group consisting of fluoro, chloro, $(C_1-C_6)$alkyl, $(C_1-C_6)$ alkoxy, $(C_1-C_4)$perfluoroalkyl, $(C_1-C_4)$ perfluoroalkoxy, $(C_1-C_6)$alkylthio, $(C_1-C_6)$ alkylsulfinyl, phenylsulfonyl, $(C_1-C_6)$ alkylsulfonyl and phenylsulfonyl;

$R^2$ is hydrogen, fluoro, chloro, $(C_1-C_6)$alkyl, $(C_1-C_6)$alkoxy, $(C_1-C_4)$perfluoroalkyl, $(C_1-C_4)$perfluoroalkoxy, $(C_1-C_6)$ alkylthio, $(C_1-C_6)$alkylsulfinyl, phenylsulfinyl, $(C_1-C_6)$ alkylsulfonyl or phenylsulfonyl;

with the provisos that:
$G^1$ and $G^2$ are not hydroxy at the same time;
$G^3$ and $G^4$ are not hydroxy at the same time;
$G^5$ and $G^6$ are not hydroxy at the same time;
$R^1$ is not phenyl substituted with carboxy, tetrazolyl or $-CO-NH-SO_2-X^7$ when $R^1$ is in the 1-position or 2-position; and
$R^1$ is not carboxy, cis or trans $-(CH_2)_m-CX^1=CX^2-CO_2H$, $-(CH_2)_m CX^3X^4X^5$ or

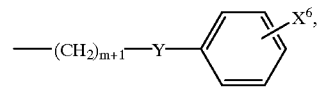

where $X^6$ is carboxy, tetrazolyl or $CH_2OH$, when $R^1$ is in the 1-position or 2-position.

DETAILED DESCRIPTION OF THE INVENTION

The term "$(C_1-C_6)$ alkyl" whenever used in the disclosure and appendant claims herein denotes saturated monovalent straight or branched aliphatic hydrocarbon radicals having one to six carbon atoms, such as methyl, ethyl, propyl, t-butyl, hexyl, etc. Similarly, the terms $C_3-C_7$ cycloalkyl and $C_3-C_8$ cycloalkyl denote a cycloalkyl group having from three to seven or eight carbon atoms, respectively, such as cyclopropyl, cyclohexyl, cyclooctyl, etc.

When $A^1$ is oxygen and $A^2$ is a substituted methylene in a compound of formula I, the compound may be described either as a 3,4-dihydrobenzopyran or a chromane.

The compounds of the invention have two asymmetric carbon atoms indicated by asterisks in the following formula:

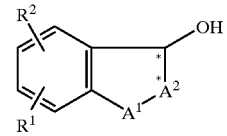

The stereo isomers may be designated with reference to R and S rotation in accordance with standard nomenclature. When reference is made herein to S,R, or R,S, a single enantiomerically pure compound is meant, whereas S*, R* and R*, S* denote a racemic mixture. The invention includes the racemic mixtures and optical isomers of formula I.

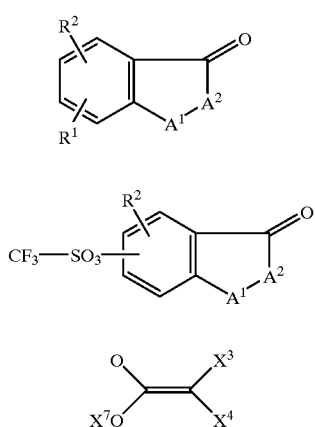

According to a specific method of the invention, compounds of formula I, wherein $R^1$ is $-(CH_2)_mCX^3X^4X^5$, where $X^3$ and $X^4$ are as defined as above for formula (I), m is 0 and $X^5$ is carboxy or the esters thereof, are prepared by reacting compounds of above formulae III and IV to form a compound of the formula V which is a compound of formula III wherein the $CF_3SO_3$ moiety has been replaced with $-(CH_2)_mCX^3X^4CO_2X^7$, wherein m, $X^3$, $X^4$ and $X^7$ are as defined above for formula (I), followed by reduction and saponification to form certain compounds of formula I.

The reaction of compounds III and IV is generally conducted in a solvent. Suitable solvents are ether solvents such as tetrahydrofuran, diethyl ether, ethylene glycol, dimethyl ether and 1,4-dioxane, dipolar aprotic solvents such as dimethylformamide, N,N-dimethylacetamide, acetonitrile, dimethyl sulfoxide, hexamethylphosphoramide, N,N-dimethylpropylene urea, non-polar aromatic solvents such as xylene, benzene, chlorobenzene and toluene, and halogenated solvents such as methylene chloride, chloroform and dichloroethane. Specific suitable solvents are xylene, or a mixture of equal volumes of ethylene glycol, dimethylether and dimethyl formamide. The reaction temperature ranges from −78° C. to 200° C. depending on the boiling point of the solvent used and usually ranges from about 80° to about 150° C.

The reaction may be carried out in the presence of a Lewis acid such as zinc chloride, aluminum chloride, magnesium bromide, tin chloride or titanium chloride. When present, the amount of Lewis acid ranges from about 0.05 to about 2 equivalent per mole of compound III.

The reaction is generally carried out with a palladium catalyst. Suitable palladium catalysts are tetrakistriphenylphosphine palladium, bis-benzonitrile palladium chloride, allyl palladium chloride dimer, palladium chloride, palladium acetate, palladium on carbon, and bisacetonitrile palladium chloride. A specific catalyst comprises 5% by weight allyl palladium chloride dimer or 5% by weight bisbenzonitrile palladium chloride. Generally, about 0.001 equivalent to one equivalent of catalyst per mole of substrate is used.

The reaction is generally carried out in the presence of a phosphine ligand such as triphenylphosphine, tri-o-tolylphosphine or tri-2-furylphosphine in an amount of about 0.1 to about 5, preferably 1 to 2 molar equivalents per mole of substrate used.

The reduction of the compound of the formula V is carried out in a conventional manner with sodium borohydride in an alcohol solvent at ambient temperature to form certain compounds of formula I.

The compounds of formula III wherein $R^5$ is $-(CH_2)_nCHX^9X^{10}$ or $-(CH_2)_nX^{10}$, wherein n, $X^9$, and $X^{10}$ are defined as above for formula I, may be prepared as described hereinbelow from compounds of the formula VI

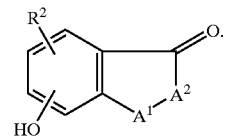

A compound of formula VI, wherein $A^1$, $A^2$ and $R^2$ are as defined above for formula I, is reacted with trifluoromethane sulfonic anhydride (also called triflic anhydride) in a suitable solvent such as methylene chloride in the presence of triethylamine to form the corresponding triflate compound.

The group $R^5$ when defined as $-(CH_2)_nCHX^9X^{10}$ or $-(CH_2)_nX^{10}$ may be introduced into the triflate compound by a two step procedure comprising reacting it with an aldehyde of the formula $X^9X^{10}CH(CH_2)_{n-1}CHO$ or $X^{10}(CH_2)_{n-1}CHO$ to form the corresponding alkene compound and then hydrogenating. The reaction with the aldehyde is conducted in the presence of a pyrrolidine catalyst or with hydrochloric acid catalyst in acetic acid. The hydrogenation is carried out with hydrogen and a palladium catalyst in a conventional manner.

The compounds of formula VI are generally commercially available. If not, they may be obtained by methods well known to those skilled in the art. For instance, the compounds of formula VI wherein $A^1$ is oxygen and $A^2$ is

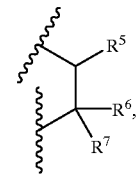

wherein $R^5$, $R^6$ and $R^7$ are as defined above for formula I, may be obtained from $R^2$-substituted 2',4'-dihydroxy-3-chloropropiophenone (hereafter compound 1), wherein $R^2$ is as defined above for formula I, by cyclization with sodium hydroxide. Compound 1 may be prepared from $R^2$-substituted resorcinol, wherein $R^2$ is as defined above for formula (I), and 3-chloropropionic acid in the presence of an acid, preferably trifluoromethane sulfonic acid.

The compounds of formula VI wherein $A^1$ is sulphur and $A^2$ is

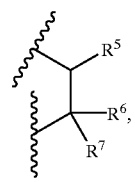

wherein $R^5$, $R^6$ and $R^7$ are as defined above for formula I, may similarly be obtained from $R^2$ -substituted 4' or 5'-hydroxy-2'-sulfhydryl-3-chloro-propiophenone, wherein $R^2$ is as defined above for formula I, which, in turn, may be obtained from $R^2$-substituted 3-hydroxythiophenol.

The compounds of formula VI wherein $A^2$ is

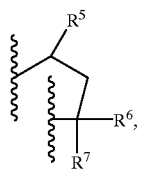

wherein $R^5$, $R^6$ and $R^7$ are as defined above for formula I, and $A^1$ is O or S may similarly be obtained by reaction of $R^2$-substituted resorcinol or 3-hydroxythiophenol, respectively, wherein $R^2$ is as defined above for formula I, and 4-chlorobutyric acid, and cyclization with sodium hydroxide.

The compounds of formula III where $R^6$ or $R^7$ are not H are prepared from generally available or known compounds of formula V which are protected as the benzyl ethers under standard conditions and reacted with aldehydes of the formula $CHO(CH_2)_{u-1}CHX^9X^{10}$ or $CHO(CH_2)_{u-1}X^{10}$ wherein $X^9$ and $X^{10}$ are as defined above for formula I and u is 1, 2, 3 or 4, in the presence of $Si(OCH_3)_4$ and $Cs_2CO_3$ in DMF as described in the literature to form the corresponding alkene compounds.

The group $R^5$ when defined as $—O(CH_2)_qCHX^9X^{10}$ or $—O(CH_2)_qX^{10}$, wherein q, $X^9$ and $X^{10}$ are as defined above for formula I, may be introduced into a compound of the formula II, wherein $R^1$, $R^2$, and $A^1$ are as defined above for formula I and $A^2$ is

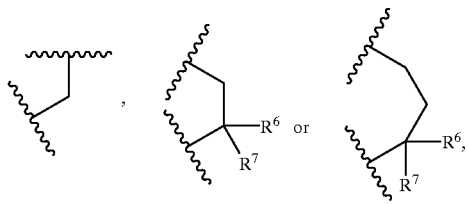

by the procedure outlined below.

The compounds of formula X

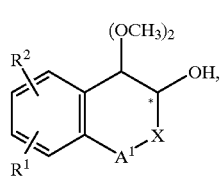

(X)

wherein $R^1$, $R^2$, and $A^1$ are as defined above for formula I and X is a covalent bond,

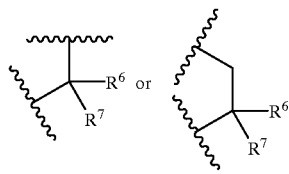

may be prepared from the compounds of formula IX by mixing such compounds with 20% potassium hydroxide and adding phenyldiacetoxy iodide.

The compounds of formula X when combined with $Br(CH_2)_qCHX^9X^{10}$, or $Br(CH_2)_qX^{10}$, wherein q, $X^9$ and $X^{10}$ are as defined above for formula I, form the corresponding ether compounds which are then deprotected by hydrolysis with an acid such as hydrochloric acid to give the corresponding ketone compounds. The ketone compounds upon reduction, as described above for the reduction of the compound of formula V, form compounds of the formula I.

The compounds of formula III wherein $R^5$ is as defined above for formula I may be converted into compounds of formula I wherein $R^1$ is $(CH_2)_mCX^1=CX^2—CO_2H$, where m, $X^1$ and $X^2$ are as defined above for formula I, in accordance with the following reaction sequence.

A compound of formula III is reacted with $(CH_3)_3SnSn(CH_3)_3$ and a palladium catalyst such as tetrakistriphenylphosphine palladium $(Pd(PPh_3)_4)$ in the presence of a phosphine ligand, as described above for the reaction of compounds of the formulae III and IV, to form the corresponding trimethyltin compound. The trimethyltin compound is reacted with an ester-protected compound of the formula $X^7O_2CX^2C=CX^1—(CH_2)_mZ$, wherein $X^1$, $X^2$, $X^7$ and m are as defined above for formula I and Z is iodo, bromo or $CF_3SO_3$, to form the corresponding ketone ester compound wherein $X^7O_2CX^2C=CX^1(CH_2)_m—$ has displaced the trimethyltin moiety. The coupling reaction proceeds in the presence of a palladium catalyst, such as bis-triphenylphosphine palladium chloride, as described above.

The ketone ester compounds are reduced to the corresponding hydroxyl compounds and then hydrolyzed to the corresponding acid of formula I. The reduction proceeds with sodium borohydride. Generally, the reduction is carried out in a solvent. Suitable solvents are lower alcohols having one to six carbon atoms, mixtures of lower alcohols with organic solvents such as tetrahydrofuran or dioxane, and mixtures of water-miscible lower alcohols or other water-miscible organic solvents with water. The solvent is preferably a lower alcohol such as methanol or ethanol. The reaction temperature generally ranges from about $-78°$ C. to about $100°$ C., and usually from about $0°$ C. to about $25°$ C.

The reduction step results in a stereoisomeric mixture of the ester compounds of formula I having the following structures:

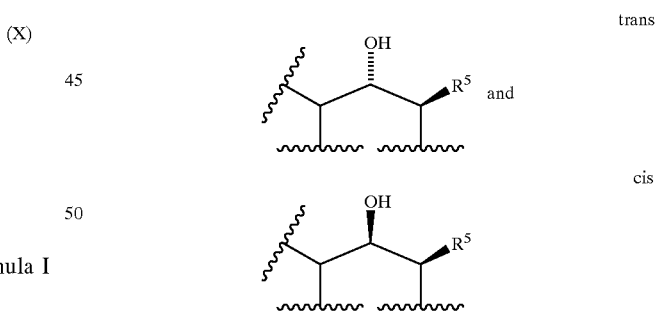

These cis and trans isomers may be separated by conventional column chromatography.

Compounds of formula I wherein $R^1$ is carboxy and $R^2$ is hydrogen may be prepared from intermediate compounds of the formula III by first replacing the $CF_3SO_3$-group by methoxycarbonyl, and then hydrolyzing. The replacement reaction proceeds with carbon monoxide in the presence of palladium acetate, 1,1'-bis(diphenylphosphine)ferrocene (DPPF), methanol and triethylamine. The hydrolysis is as previously described.

Compounds of formula I wherein $R^1$ is $—(CH_2)_m CX^3X^4X^5$, wherein m, $X^3$, $X^4$ and $X^5$ are as defined above for formula I, will be designated hereafter as compounds of the formula XXI (not shown). Although the following chemistry describes the preparation of compounds wherein $R^1$ is —$(CH_2)_m CX^3 X^4 CO_2 C_2 H_5$, it will be readily understood by one skilled in the art that the same chemistry applies to compounds having a different $R^1$ than —$(CH_2)_m CX^3 X^4 CO_2 C_2 H_5$, as defined for formula I, which are inert under the reaction conditions specified below.

The starting material of formula XVI is a compound of formula II above, wherein $R^1$ is —$(CH_2)_m CX^3 X^4 X^5$ where $X^5$ is a carboxy ethyl ester and m is 0. Preparation of this starting material is described above.

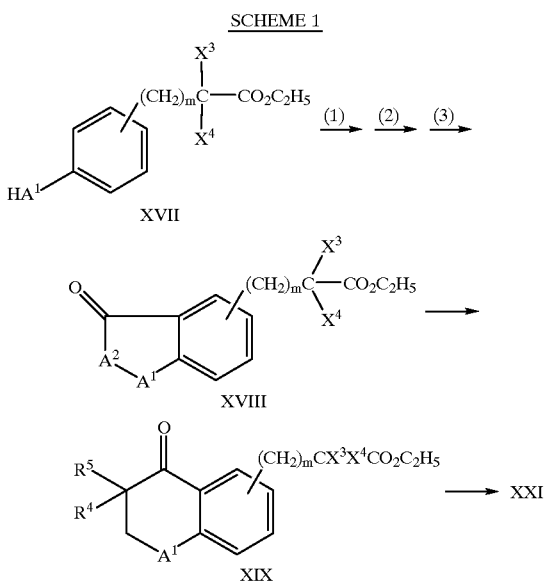

Compounds of formula XVII are converted by subsequent reactions with (1) acrylonitrile, (2) hydrolysis with concentrated hydrochloride, and (3) cyclization with polyphosphoric acid to form the compound of formula XVIII. Introduction of group $R^5$ to form compounds of formula XIX is as described hereinabove. The hydrogenation and hydrolysis of the compound of formula XIX is as described hereinabove.

Compounds of formula XVII may be prepared from 3-hydroxyphenyl acetic acid by introduction of groups $X^3$ and $X^4$ by known methods.

The starting material XVI, when m is 0, 1 or 2, $A^2$ is

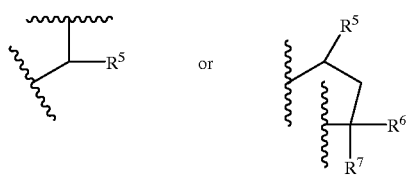

and $A^1$ is O, S, NH, or N($C_1$–$C_6$)alkyl may be prepared by reacting the compound of formula XVII with $BrCH_2CN$ or $BrCH_2CH_2CH_2CN$ in step (1) of Scheme I and reacting further as described with reference to Scheme I.

The starting material XVI wherein $A^1$ is $CH_2$, m is 0, 1 or 2, and $A^2$ is

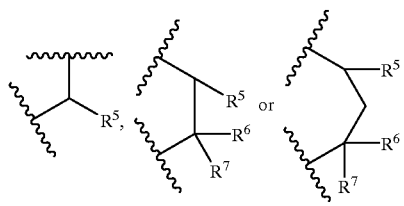

may be prepared as described below.

A benzene substituted with —$(CH_2)_m$—$CX^3 X^4 CO_2 C_2 H_5$, wherein m, $X^3$ and $X^4$ are as defined above for formula I, is reacted with a mono acid chloride mono ester of malonic, succinic or glutaric acid in the presence of a Friedel Crafts catalyst such as aluminum chloride. The resulting ketone is converted to the corresponding propylene dithiol with propylene dithiol and boron trifluoride catalyst. The formed compound is reduced with Raney nickel and then saponified. The ring is formed with polyphosphoric acid to produce the bicyclic compound XIX. Introduction of group $R^5$ is as described hereinabove.

Compounds of formula XXI, wherein $X^5$ is $CO_2H$ may be prepared by saponification of a compound of formula I where $R^1$ is —$(CH_2)_m CX^3 X^4 CO_2 CH_3$, where m, $X^3$ and $X^4$ are as defined above for formula I, the preparation of which is described above.

Compounds of formula XXI, wherein $X^5$ is OH; m is 0, 1 or 2; and $X^3$ and $X^4$ are each hydrogen may be prepared by conventional lithium aluminum hydride hydrogenation of a compound of formula I wherein $R^1$ is —$(CH_2)_m CO_2 CH_3$, where m is 0, 1 or 2.

Compounds of formula XXI, wherein $X^5$ is OH; m is 0, 1 or 2, and $X^3$ and $X^4$ are each alkyl may be prepared by reacting the corresponding compounds wherein $X^3$ and $X^4$ are hydrogen with one equivalent of a Grignard reagent containing group $X^3$, e.g. $X^3MgCl$, followed by one equivalent of a Grignard reagent containing group $X^4$, e.g. $X^4MgCl$.

Compounds of formula XXI, wherein $X^5$ is OH; m is 0, 1 or 2, and $X^3$ and $X^4$ are taken together to form $C_3$–$C_7$ cycloalkyl are similarly prepared by reacting the corresponding compounds wherein $R^4$ and $R^5$ are hydrogen with a Grignard reagent derived from a $C_3$–$C_7$ dihalo alkane, e.g. $ClMg(C_3$–$C_7$ alkanyl)$MgCl$.

Compounds of formula I wherein $R^1$ is

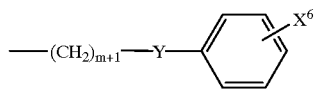

where $X^6$ is carboxy, tetrazolyl, —$CONG^5G^6$ wherein $G^5$ and $G^5$ are as defined above for formula I, or $CH_2OH$; Y is O, S, NH or NH($C_1$–$C_6$ alkyl); and m is 0, 1 or 2, may be prepared by reacting a compound of the formula

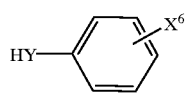

with a triflate compound of the formula I wherein $R^1$ is $CF_3SO_3CH_2(CH_2)_m$— in the presence of a base such as triethyl amine or sodium hydride in a reaction inert solvent.

The triflates may be prepared by reacting triflic anhydride with the compound of formula XXI wherein m is 0, 1 or 2;

$X^3$ and $X^4$ are hydrogen; and $X^5$ is hydroxyl, the synthesis of which is described above.

The compounds of formula I wherein $R^1$ is —$CONG^1G^2$, where $G^1$ and $G^2$ are as defined above for formula I, may be prepared by taking the corresponding compound wherein $R^1$ is carboxy and reacting it with an amine of the formula $NHG^1G^2$.

SCHEME II

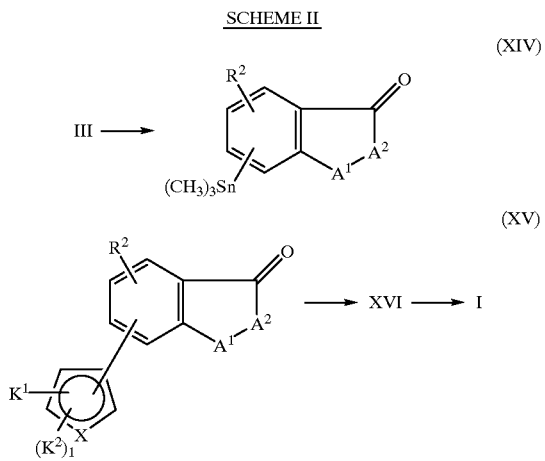

Compounds of formula XIV, wherein $A^1$, $A^2$ and $R^2$ are as defined above for formula I, are formed by reaction of compounds of formula III with $(CH_3)_3SnSn(CH_3)_3$ and a palladium catalyst such as tetrakistriphenylphosphine palladium ($Pd(PPh_3)_4$), or bisbenzonitrile palladium chloride, in the presence of a phosphine ligand, such as triphenylphosphine, in an amount of about 0.1 to about 5 molar equivalent per mole of substrate used. Compounds of formula XIV are converted to a compound of formula XV by reaction with an ester-protected compound of the formula

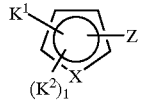

wherein X is C, CH, N, O or S; $K^1$ is carboxy, tetrazolyl, —CO—N(H)($SO_2$—$X^7$), —N(H)($SO_2$—$X^7$), —N(H)(CO—$X^7$) or —N(H)(CO—O$X^7$); $K^2$ is F, Cl, ($C_1$–$C_6$)alkyl, ($C_1$–$C_6$)alkoxy, ($C_1$–$C_4$)perfluoroalkyl, ($C_1$–$C_4$)perfluoroalkoxy, ($C_1$–$C_6$)alkylthio, ($C_1$–$C_6$)alkylsulfinyl, phenylsulfinyl, ($C_1$–$C_6$)alkylsulfonyl or phenylsulfonyl, l is 1 or 2 and Z is iodo, bromo or $CF_3SO_3$. The coupling reaction proceeds in the presence of a palladium catalyst, such as tetrakistriphenylphosphine palladium or bistriphenylphosphine palladium chloride.

The hydroxy esters of formula XVI are also prepared by the method described in Scheme III (shown below) where the oxazoline containing compound XXII or its heteroaromatic analogs as defined previously are treated with an alkyl lithium reagent, preferably n-BuLi, at a temperature of –20° C. to –78° C., preferably –78° C. in an inert solvent, such as toluene, ether, tetrahydrofuran or methylene chloride, preferably toluene, to provide an intermediate aryl lithium reagent (not shown). The intermediate is then treated with $ZnCl_2$ (in a solution of ether or neat) to afford the aryl zinc reagent XXIII. The aryl zinc reagent is reacted, without isolation, with compounds of formula III in the presence of a catalytic amount of a catalyst, particularly a palladium catalyst which is any palladium source which provides palladium ($Pd^0$) under the reaction conditions such as tetrakistriphenylphosphine palladium. The reaction is usually carried out at or about the reflux temperature of the solvent used, preferably at about 75° C. The reaction time is generally about 1 to 24 hours, preferably about 3 hours to form the oxazoline ketone XXIV.

The oxazoline containing ketone XXIV is reduced with $NaBH_4$ under standard conditions. The cis and trans isomers are separated and the mixture of enantiomers resolved as described previously for the hydroxy esters. Cleavage of the oxazoline moiety can be accomplished by treatment of the hydroxy analog XXV with excess methyl iodide at 23° C. to reflux temperature for 1 to 3 days, preferably 2 days. The solid iminium salt is isolated by evaporation of the excess methyl iodide and saponified with an alkaline metal base in water or mixture of water and a miscible cosolvent such as a lower alcohol or THF, preferably methanol. The acid XXVI, wherein $R^2$, $A^1$ and $A^2$ are as defined above for formula I, is used directly as an intermediate or esterified with ethyl or methyl iodide in the presence of an inorganic base preferably $K_2CO_3$ in a solvent such as acetone, acetonitrile or DMF, preferably acetone, to give the corresponding esters XVI.

SCHEME III

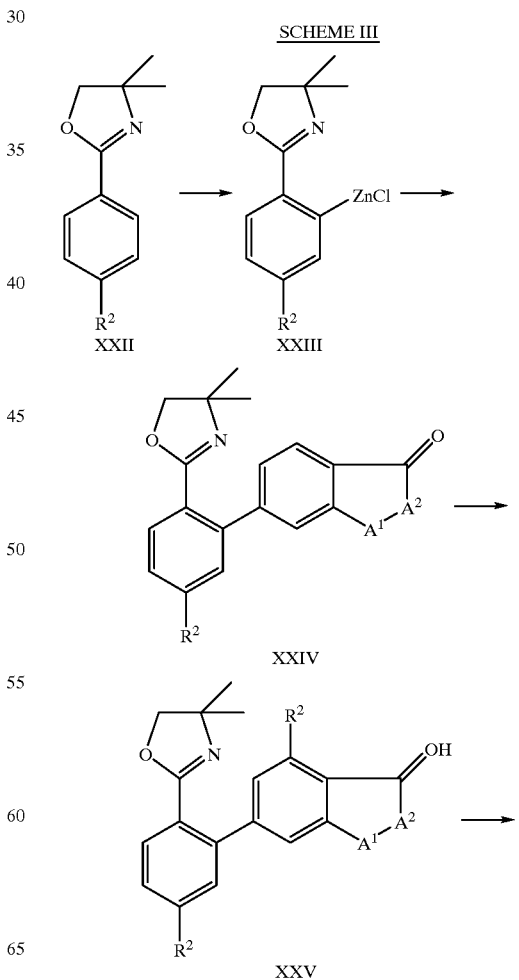

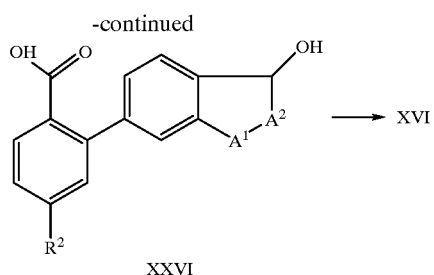

XXVI

The ketone esters of formula XV are first reduced to the corresponding hydroxyl compounds XVI (formula not shown) and then hydrolyzed to the corresponding acid of formula I. The reduction proceeds with sodium borohydride, as described above with reference to the reduction of the ketones of formula II.

Resolution of the enantiomeric mixture resulting after separation of the cis and trans isomers may be accomplished by methods known in the art. In one method, a compound of formula I wherein $R^1$ contains a carboxyl group (COOH) is reacted with a chiral base such as d-ephedrine in a polar solvent such as ether to form diastereomeric salts which are separated and then converted into optically pure acids by treatment with an acid such as aqueous or methanolic hydrogen chloride. In another method, a compound of formula I wherein $R^1$ contains a carboxylic acid ester group is reacted with an optically active acid such as R-mandelic acid or N-t-butoxycarbonyl-D-tryptophan to form diastereomeric esters with the hydroxyl group which, after separation, are converted into optically pure acids by treatment with a base such as sodium hydroxide in methanol or ethanol. Removal of the resolving ester group and hydrolysis of the carboxylic acid ester group in $R^1$ is conveniently carried out with aqueous base such as an alkali metal hydroxide, e.g. sodium hydroxide, at temperatures ranging from about room temperature to the reflux temperature of the solvent or solvent mixture used. The reaction may be conducted in the presence of a co-solvent such as methanol, ethanol or tetrahydrofuran.

The compounds of formula I where $X^6$ of $R^1$ or aromatic substitution is equal to $N(H)(CO—X^7)$, $N(H)(SO_2—X^7)$ or $N(H)(CO—OX^7)$ may be obtained by reaction of compounds of formula I where $X^1$ or $x^6$ of $R^1$ is carboxy or substituted aromatic or heteroaromatic acid with diphenylphosphoryl azide in a solvent such as toluene, DME, THF, dichloroethane in the presence of benzyl alcohol and an amine base such as pyridine, diisopropylethyl amine, pyrrolidine or, preferably, triethyl amine at the temperature of the boiling point of the solvent used for a time of 5–48 hours, preferably 16 hours. The product from this reaction is hydrogenated in a lower alcohol solvent in the presence of a palladium catalyst, preferably $Pd(OH)_2/C$, followed by acylation with the appropriate acid chloride, carbamoyl chloride or sulfonyl chloride.

The synthetic methods outlined above together with the following examples describe methods which were and can be employed to prepare the compounds of this invention.

Where possible, as ascertained by one skilled in the art enabled by this disclosure, pharmaceutically acceptable cationic salts of certain compounds of this invention include but are not limited to, those of sodium, potassium, calcium, magnesium, ammonium, N,N'-dibenzylethylenediamine, N-methylglucamine, ethanolamine and diethanolamine. The pharmaceutically acceptable cationic salts of the compounds of formula I can be prepared by mixing a compound of formula I with one equivalent of an amine base or alkaline metal base.

The compounds of the invention can be administered to mammals, including humans, for the treatment of $LTB_4$ induced illnesses by various routes including oral, parenteral and topical, including the use of suppositories and enemas. On oral administration, dosage levels of about 0.5 to 1000 mg/day, more preferably about 5–500 mg/day, may be given in a single dose or up to 3 divided doses. For intravenous administration, dosage levels are about 0.1–500 mg/day, more preferably about 1.0–100 mg/day. Intravenous administration can include a continuous drip. Variations will necessarily occur depending on the age, weight and condition of the subject being treated and the particular route of administration chosen as will be known to those skilled in the art enabled by this disclosure.

The compounds of the invention may be administered alone, but will generally be administered in admixture with a pharmaceutical carrier or diluent selected with regard to the intended route of administration and standard pharmaceutical practice well known to those skilled in the art. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic.

The $LTB_4$ activity of the compounds of the invention may be determined by comparing the ability of the compounds of the invention to compete with radiolabelled $LTB_4$ for specific $LTB_4$ receptor sites on guinea pig spleen membranes. Guinea pig spleen membranes are prepared as described by Cheng et al. (J. Pharmacology and Experimental Therapeutics 232:80, 1985). The $^3H$-$LTB_4$ binding assay is performed in 150 $\mu$L containing 50 mM Tris pH 7.3, 10 mM $MgCl_2$, 9% methanol, 0.7 nM $^3H$-$LTB_4$ (New England Nuclear, approximately 200 Ci/mmol) and 0.33 mg/ml guinea pig spleen membranes. Unlabeled $LTB_4$ is added at a concentration 5 $\mu$M to determine non-specific binding. Compounds are added at varying concentrations to evaluate their effects on $^3H$-$LTB_4$ binding. The reactions are incubated at 4° C. for 30 minutes. Membrane bound $^3H$-$LTB_4$ is collected by filtration through glass fiber filters and the amount bound is determined by scintillation counting. The $IC_{50}$ value for a compound is the concentration at which 50% of specific $^3H$-$LTB_4$ binding is inhibited.

The functional activity of the compounds of the invention may be determined in several ways using bioassays. Both high and low affinity forms of the $LTB_4$ receptor have been described that differentially couple to leukocyte chemotaxis and adhesion molecule upregulation respectively (Sterman, J. W.; Groetzl, E. J. et al., J. Immun., 1988, 140, 3900–3904). Human neutrophil chemotaxis is measured as described in Horvath, L. et al., J. Immunol. 1987, 139, 3055. Human neutrophil CD11 b upregulation is measured as described in Marder, P. et al., Prostaglandins, Leukotriene Essent. Fatty Acids, 1991, 46, 265–278.

In addition, compounds of formula I can be tested in vivo according to a method analogous to the method described by Pettipler, E. R. et al., Brit. J. Pharmacology, 1993, 423–427, by injecting $LTB_4$ into the dermis of guinea pigs and measuring the blockade of neutrophil migrations into the skin by orally dosed compounds of formula I.

The following Examples illustrate the preparation of the compounds of the ethanolamine and diethanolamine. The pharmaceutically acceptable cationic salts of the compounds of formula I can be prepared by mixing a compound of formula I with one equivalent of an amine base or alkaline metal base.

The compounds of the invention can be administered to mammals, including humans, for the treatment of $LTB_4$ induced illnesses by various routes including oral, parenteral and topical, including the use of suppositories and enemas. On oral administration, dosage levels of about 0.5 to 1000 mg/day, more preferably about 5–500 mg/day, may be given in a single dose or up to 3 divided doses. For intravenous administration, dosage levels are about 0.1–500 mg/day, more preferably about 1.0–100 mg/day. Intravenous administration can include a continuous drip. Variations will necessarily occur depending on the age, weight and condition of the subject being treated and the particular route of administration chosen as will be known to those skilled in the art enabled by this disclosure.

The compounds of the invention may be administered alone, but will generally be administered in admixture with a pharmaceutical carrier or diluent selected with regard to the intended route of administration and standard pharmaceutical practice well known to those skilled in the art. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic.

The $LTB_4$ activity of the compounds of the invention may be determined by comparing the ability of the compounds of the invention to compete with radiolabelled $LTB_4$ for specific $LTB_4$ receptor sites on guinea pig spleen membranes. Guinea pig spleen membranes are prepared as described by Cheng et al. (J. Pharmacology and Experimental Therapeutics 232:80, 1985). The $^3H$-$LTB_4$ binding assay is performed in 150 µL containing 50 mM Tris pH 7.3, 10 mM $MgCl_2$, 9% methanol, 0.7 nM $^3H$-$LTB_4$ (New England Nuclear, approximately 200 Ci/mmol) and 0.33 mg/ml guinea pig spleen membranes. Unlabeled $LTB_4$ is added at a concentration 5 µM to determine non-specific binding. Compounds are added at varying concentrations to evaluate their effects on $^3H$-$LTB_4$ binding. The reactions are incubated at 4° C. for 30 minutes. Membrane bound $^3H$-$LTB_4$ is collected by filtration through glass fiber filters and the amount bound is determined by scintillation counting. The $IC_{50}$ value for a compound is the concentration at which 50% of specific $^3H$-$LTB_4$ binding is inhibited.

The functional activity of the compounds of the invention may be determined in several ways using bioassays. Both high and low affinity forms of the $LTB_4$ receptor have been described that differentially couple to leukocyte chemotaxis and adhesion molecule upregulation respectively (Sterman, J. W.; Groetzl, E. J. et al., J. Immun., 1988, 140, 3900–3904). Human neutrophil chemotaxis is measured as described in Horvath, L. et al., J. Immunol. 1987, 139, 3055. Human neutrophil CD11b upregulation is measured as described in Marder, P. et al., Prostaglandins, Leukotriene Essent. Fatty Acids, 1991, 46, 265–278.

In addition, compounds of formula I can be tested in vivo according to a method analogous to the method described by Peftipler, E. R. et al., Brit. J. Pharmacology, 1993, 423–427, by injecting $LTB_4$ into the dermis of guinea pigs and measuring the blockade of neutrophil migrations into the skin by orally dosed compounds of formula I.

The following Examples illustrate the preparation of the compounds of the invention and are not to be construed as limiting the scope of this invention in any way.

EXAMPLE 1

(3S,4R)-7-(2-Trifluoromethanesulfonylamine-5-fluorophenyl)4-hydroxy-3-phenylmethyl-2H-1-benzopyran A. 2',4'-Dihydroxy-3-chloropropiophenone To a stirred mixture of resorcinol (200 9, 1.82 mol) and 3-chloropropionic acid (200 g, 1.84 mol) was added trifluoromethane sulfonic acid (1 kg) in one portion. The solution was heated slowly over about 45 minutes at about 80° C. then cooled to room temperature over about 15 minutes and poured into chloroform (4.0 L). The organic portion was slowly poured into water (4.0 L) and the layers separated. The aqueous layer was extracted with chloroform (2×2.0 L). The combined organic layers were washed with brine, dried over sodium sulfate and filtered. Concentration in vacuo gave an orange semi-solid (244.1 g) which was used crude in the next step. $^1H$-NMR (300 MHz, $CDCl_3$): 12.56 (1H, s), 7.63 (1H, d, J=7.6 Hz), 6.37–6.46 (2H, m), 3.92 (2H, t, J=6.3 Hz), 3.41 (2H, t, J=6.3 Hz).

B. 7-Hydroxybenzopyran4-one

To a cooled (about 5° C.) solution of 2N sodium hydroxide (10.0 L) was added the compound of Example 1A (244.1 g) in one portion. The solution was warmed to room temperature over about 2 hours using a warm water bath then recooled to about 5° C. and the pH adjusted to 2 with 6M sulfuric acid (1.2 L). The mixture was extracted with 3×3.0 L of ethyl acetate, washed with brine (1×2.0 L) dried over sodium sulfate and filtered. Concentration in vacuo gave a tan solid. Trituration with hexanes, and filtration afforded 173.7 g (58% yield) of the title compound of this Example 1 B. M.P. 136° C.137° C.

C. 7-[Trifluoromethylsulfonyloxy]-benzopyran-4-one

To a stirred solution of the compound of Example 1B (173.7 9, 1.05 mole) in methylene chloride (3.0 L) at about −78° C. was added triethylamine (320 g, 3.16 mole) and dimethylaminopyridine (2.5 g). After total dissolution, trifluoromethane sulfonic anhydride (327 g, 1.16 mole) was added dropwise over about 20 minutes, the material was stirred for about 30 minutes at about −78° C., and then warmed to room temperature over about 2 hours. The reaction mixture was poured into saturated ammonium chloride solution (2.5 L) and the layers separated. The aqueous layer was extracted with 2×2.0 L of methylene chloride. The combined organic fractions were washed with water (1×1.0 L), dried over magnesium sulfate and filtered. Concentration in vacuo gave a red oil. Chromatography over silica gel (1 kg) eluting with (8:1) hexane:ethyl acetate gave, after solvent removal, 211.1 g. (69% yield) of the title product. M.P. 43–44° C.

D. 7-[(Trifluoromethylsulfonyl)oxy]-3-phenylmethylene-benzopyran-4-one

To a stirred solution of the product of Example 1C (27 g, 91.2 mmole) in 183 mL of methanol was added benzaldehyde (11.1 mL, 109 mmole) followed by pyrrolidine (9.1 mL, 109 mmole). The mixture was stirred at room temperature overnight, cooled to about 0° C. and filtered. The solid was washed once with 50 mL of ice-cold methanol a[]nd then dried in vacuo; 35.2 g, (75% yield) of the title product of this Example 1D was recovered. M.P. 133–135° C. $^1H$ NMR (300 MHz, CDCl$_3$): 8.11 (1H, J, J=8.7 Hz), 7.91 (1H, bs), 7.40–7.51 (2H, nm), 7.24–7.38 (3H, m), 6,97 (1H, dd, J=8.7 Hz, 2.4 Hz), 6.91 (1H, d, J=2.4 Hz), 5.40 (1H, bs).

E. 7-[(5-Fluoro-(2-(4,4-dimethyl-2-oxazolinyl)phenyl]-3-phenylmethylene-1-benzopyran-4-one To a stirred solution of 2-(4-fluorophenyl)4,4-dimethyl-2-oxazoline (1.0 eq in tetrahydrofuran, 0.5M concentration) at about −78° C. under N$_2$ was added n-butyllithium in hexanes (1.1 eq., 2.5M solution). The mixture was stirred at about −78° C. for about 1 hour, then ZnCl$_2$ (1M solution in ether, 1.1 eq.) was added. The mixture was warmed to about 10° C. over about 1 hour to give 2-(4-fluorophenyl-2-chlorozinc)4,4-diethyl-2-oxazoline (not isolated). To this solution was added 7-[((trifluoromethyl)sulfonyl)oxy]-3-phenylmethylene-1-benzopyran-4-one (1.0 eq.) and Pd(PPh$_3$)$_4$ (0.02 eq.). The mixture was refluxed (about 68° C.) for about 3 hours, cooled to room temperature and poured into NH$_4$Cl solution. The solution was extracted 3 times with diethyl ether and the combined organic fraction dried over MgSO$_4$. Filtration followed by solvent removal in vacuo and column chromatography (silica gel—2:1 hexane:ether) gave the title compound of this Example 1F as a yellow solid, 65% yield, m.p. 110–112° C. $^1$H-NMR (300 MHz, CDCl$_3$): 8.04 (1H, d), 7.91 (1H, s), 7.78 (1H, dd), 7.41–7.52 (3H, m), 7.31 (2H, d), 7.06–7.18 (3H, m), 7.02 (1H, s), 5.40 (2H, s), 3.86 (2H, s), 1.31 (6H, s).

F. (3S*,4R*)7-[5-Fluoro-(2-(4,4-dimethyl-2-oxazolinyl)phenyl]-4-hydroxy-3-phenylmethyl-2H-1-benzopyran To a stirred solution of the compound from Example 1E in THF (0.1M) at about 0° C. was added LiAlH$_4$ (1M in ether, 2.2 eq) dropwise over about 10 minutes. The mixture was warmed to room temperature and stirred for about 12 hours. The mixture was cooled to about 0° C., quenched with Rochelles salt, and filtered through diatomaceous earth. The aqueous layer was extracted twice with ethyl acetate, and the combined organic layers were washed with brine and dried over MgSO$_4$. Filtration and solvent removal afforded a yellow oil. Chromatography over silica gel (ethyl acetate:hexane) afforded a 60% yield of a white solid. M.P. 65–70° C. (decomposed). Anal. calcd. for C$_{27}$H$_{26}$NO$_3$F: C, 75.15; H, 6.07; N, 3.25. Found: C, 74.75, H, 6.02, N, 3.09. $^1$H-NMR (300 MHz, CDCl$_3$): 7.70 (1H, dd), 7.02–7.37 (8H, m), 6.96 (1H, dd), 7.91 (1H, d), 4.51 (1H, d), 4.23 (1H, dd), 4.39 (1H, dd), 3.87 (2H, c'd), 2.74 (1H, dd), 2.55 (1H, dd), 2.18–2.28 (1H, m), 1.31 (6H, d).

G. (3S*,4R*)7-(2-Carboxy-5-fluorophenyl)-4-hydroxy-3-phenylmethyl-2H-1-benzopyran The compound from step 1F is dissolved in methyl iodide (0.5M) at room temperature and stirred for about 24 hours. The methyl iodide was removed in vacuo, the oily solid was dissolved in CH$_2$Cl$_2$ and the solvent removed in vacuo. This operation was repeated to remove traces of methyl iodide. The solid was dissolved in methanol (0.5M) and 2M NaOH (0.5M) was added and the mixture was refluxed for about 5 hours, cooled to room temperature and acidified to pH 2 with 1M HCl. The mixture was extracted twice with ethyl acetate, washed with brine, and dried over MgSO$_4$. Filtration and solvent removal in vacuo, followed by chromatography (silica gel, 10:1 methylene chloride:methanol) gave the desired acid, 93% yield. $^1$H-NMR (300 MHz, CD$_3$COCD$_3$): 7.80 (1H, dd), 7.48 (1H, d), 7.18 (7H, m), 7.13 (1H, dd), 6.91 (1H, dd), 6.80 (1H, d), 4.52 (1H, d), 4.23 (1H, dd), 3.96 (1H, dd), 2.89 (1H, dd), 2.54 (1H, dd), 2.19–2.30 (1H, m).

H1. (3S,4R)-7-(2-Carboxy-5-fluorophenyl)-4-hydroxy-3-phenylmethyl-2H-1-benzopyran The compound from step 1G is dissolved in diethyl ether (0.1M) and warmed to reflux. To the solution was added dropwise S(−)methylbenzylamine (1 eq) in diethyl ether (0.1M), dropwise over about 10 minutes. The mixture was cooled to room temperature and stirred for about 48 hours. The precipitated salt was filtered then stirred again at reflux in diethyl ether (0.1M) for about 24 hours, followed by filtration. The salt (M.P.=170–173° C.) was taken up in methylene chloride and washed 3 times with 1M HCl, then once with brine, dried over MgSO$_4$, and filtered. Solvent removal in vacuo and recrystallization (1:1-hexane:ether) gave fine white crystals, more than 99.8% enantiomeric excess by HPLC analysis. [α]$_D^{25}$=+23.8, c=0.6 in CHCl$_3$. M.P.=119–121° C. Anal. Calcd. for C$_{23}$H$_{19}$O$_4$F: C, 73.01; H, 5.06. Found: C, 72.88; H, 4.76.

H2. (3R,4S)7-(2-Carboxy-5-fluorophenyl)-4-hydroxy-3-phenylmethyl-2H-1-benzopyran The filtrate from the combined salt slurries in Example 1D was washed three times with 1M HCl, once with brine, and dried over MgSO$_4$. Filtration and solvent removal gave a yellow solid. A similar procedure as described in Example 1D using R (+) methylbenzyl amine afforded the desired product. [α]$_D^{25}$=−23.4 (c=0.6 in CHCl$_3$), M.P.=118–120° C. Anal. Calcd. for C$_{23}$H$_{19}$O$_4$F: C, 73.01; H, 5.06. Found: C, 73.03; H, 4.84.

I. (3S,4R)-7-(2-Carbobenzyloxyamino-5-fluorophenyl)-4-hydroxy-3-phenyl-methyl-2H-1-benzopyran To a solution of the compound prepared in Example 1H1 (1 mmole) in 10 mL of 1,4-dioxane was added 1.05 eq of diphenylphosphorylazide, 1.1 eq of benzyl alcohol and 2.2 eq of triethylamine. The mixture was refluxed for about 16 hours, the solvent removed under vacuum and the residue chromatographed over silica gel (1:1-hexane:EtOAc) to afford the N-CBZ product (68% yield) $^1$H-NMR (300 MHz, CDCl$_3$): 8.10 (1H, bs), 7.48–7.28 (11H, m), 7.05 (1H, dt, J=7.1, 2.0 Hz), 6.97–6.83 (3H, m), 6.67 (1H, s), 5.17 (2H, s), 4.56 (1H, s), 4.27 (1H, dd, J=13.1, 1.8 Hz), 4.01 (1H, dd, J=13.2, 5.0 Hz), 2.80 (1H, dd, J=14.2, 7.0 Hz), 2.58 (1H, dd, J=14.2, 9.1 Hz), 2.40–2.22 (1H, m).

J. (3S,4R)-7-(2-Trifluoromethanesulfonylamine-5-fluorophenyl)4-hydroxy-3-phenylmethyl-2H-1-benzopyran To a solution of the compound prepared in Example 1I in 10 mL of EtOH was added 0.05 eq by weight of Pd(OH)$_2$ and the slurry was hydrogenated on a Parr® shaker apparatus at 1 Atm. for about 3 hours. The mixture was filtered through Celite® and the filtrate evaporated. The yellow oil was redissolved in CH$_2$Cl$_2$ (10 mL), cooled to about 0° C. and triethylamine (2.2 eq) added, followed by trifluoromethanesulfonic anhydride (1.1 eq). After stirring for about 2 hours, 2 eq of solid NaOMe was added, the reaction stirred for about 15 minutes, and H$_2$O added (10 mL). The mixture was adjusted to pH 2 with 0.1M HCl then extracted with 3×10 mL EtOAc. The combined organic layers were washed with brine, dried over MgSO$_4$, filtered and solvent removed under vacuum to afford a yellow semisolid. Chromatography over silica gel (1:1–10:1 EtOAc-Hexane) gave the desired sulfonamide. M.P.: 63–65° C.

EXAMPLE 2

3S,4R-7-(2-Carboxy-5-fluoro-phenyl)-4-hydroxy-3-(4-phenyl-phenylmethyl)-2H-1-benzopyran A. 7-[(Trifluoromethylsulfonyl)oxy]-3-(4-phenyl-phenylmethyl)-benzopyran-4-one To a solution of 7-[(trifluoromethylsulfonyl)oxy]-3-(4-phenyl-phenyl-methylene-benzopyran-4-one, prepared analogously to the procedure described in Example 1D (30.2 g, 69.2 mmole) in 250 mL of ethyl acetate in a 500 mL Parr® shaker flask was added 10% palladium on carbon catalyst (1.3 g). The mixture was hydrogenated at 40 psi until hydrogen uptake ceased after about 3 hours. The mixture was filtered through Celite® to remove the palladium catalyst, and chromatographed over silica gel (hexane-ether); 28.4 g (94% yield) of the title product of this Example 2A. M.P. 110° C. $^1$H NMR (300 MHz, CDCl$_3$): 8.01 (1H, d, J=8.5 Hz), 7.20–7.35 (9H, m), 6.81–6.96 (2H, m), 4.42 q), 3.75–3.86 (2H, m), 3.5 (2H, m), 3.28–3.38 (1H, dd), 2.90 (2H, s), 2.42–2.60 (2H, m), 1.39 (9H, s), 1.30 (3H, t).

F. 3S,4R-7-(2-Carboxy-5fluoro-phenyl)-4-hydroxy-3-(4-phenyl-phenylmethyl)-2H-1-benzopyran To a stirred solution of the less polar 4R,3S tryptophan ester of Example 2E (840 mg, 1.08 mmole) in 10 mL of methanol was added 10 mL of 2M NaOH solution. The mixture was refluxed for about 8 hours, cooled and acidified to a pH of 4 with 1M HCl. The cloudy emulsion was extracted with 3×20 mL of ethyl acetate, and the combined organic fractions were washed with brine and dried over MgSO$_4$. Filtration and solvent removal in vacuo afforded a yellow foam. Chromatography (silica gel—ethyl acetate:hexane:acetic acid—35:75:1) afforded 210 mg of product. $^1$H NMR (300 MHz, CDCl$_3$): 7.97 (1H, dt, J=7.8, 1.7 Hz), 6.85–7.09 (14H, m), 4.54 (1H, d, J=4.9 Hz), 4.22 (1H, dd, J=9.1, 2.5 Hz), 3.97 (1H, dd, J=9.1, 5.4 Hz), 2.72 (1H, dd, J=13.7, 6.2 Hz), 2.51 (1H, dd, J=13.7, 9.1 Hz), 2.04–2.20 (3H, m). (+) isomer.

Saponification as above of the more polar 3R,4S tryptophan-ester (700 mg) gave the 3R,4S enantiomer, $^1$H-NMR (300 MHz, CDCl$_3$): Same nmr as above. (−) isomer.

EXAMPLE 3

1-(3-(4-Phenyl-phenylmethyl)4-hydroxy-chroman-7-yl)-(2-cyclopentene)-carboxylicacid A. Ethyl-(1)-(3-(4-phenyl-phenylmethyl)4-chroman-7-yl)acetate Bis(acetonitrile)palladium(II) chloride (173 mg, 0.45 mmol)), tri-o-tolylphosphine (690 mg, 2.26 mmol), and the compound from Example 2A (2.1 g, 4.52 mmol) were dissolved in dioxane (20 mL) and stirred for about 5 minutes. One third (1.33 g, 4.57 mmol) of the total amount of ethyl trimethylsilylketene acetal was then added along with ZnCl$_2$ (2.3 mL, 1.13 mmol) and DMF (20 mL). The resulting mixture was warmed to reflux (bath ~130° C.). After about 15 minutes, a second aliquot of silylketene acetal (1.33 g, 4.57 mmol) was added (⅓ of total). After about another 30 min, the final aliquot (1.33 g, 4.57 mmol) was added and the resulting mixture stirred at reflux for about two hr. The resulting dark brown solution was cooled, quenched with sat. NH$_4$Cl solution, and extracted with CH$_2$Cl$_2$. The combined extracts were washed with brine, dried over MgSO$_4$, filtered and evaporated. Flash chromatography of the residue, eluting with 6:1 hexane-ethyl acetate, afforded 180 mg of the desired product as a light yellow, viscous oil. $^1$HNMR (300 MHz, CDCl$_3$): 7.91 (1H, d, J=8.3 Hz), 7.63–7.20 (9H, m), 6.98 (1H, d, J=8.3 Hz), 6.92 (1H, s), 4.42 (1H, dd, J=10.1, 5.1 Hz), 4.264.12 (3H, m), 3.62 (2H, s), 3.32 (1H, dd, J=14.1, 6.2 Hz), 3.05–2.88 (1H, m), 2.76 (dd, J=14.1, 10.0 Hz), 1.28 (3H, t, J=7.0 Hz).

B. Ethyl-1-(3-(4-phenyl-phenylmethyl)4-hydroxy-chroman-7-yl)acetate

To a solution of the ketone from Example 3A (0.45 mmol) in MeOH-methylene chloride (15 mL ca. 2:1) at about 0° C. was added NaBH$_4$ (17 mg, 0.45 mmol). After stirring for about 1.5 h, the reaction was quenched with NH$_4$Cl solution, extracted with CH$_2$Cl$_2$, washed with brine, dried over MgSO$_4$, filtered and evaporated. Flash chromatography, eluting with 4:1 hexane-ethyl acetate provided 160 mg of the cis-alcohol followed by 90 mg of the desired trans-alcohol as an off-white solid. trans-$^1$HNMR (300 MHz, CDCl$_3$): 7.65–7.23 (11H, m), 6.91 (1H, d, J=8.0 Hz), 6.83 (1H, s), 4.54 (1H, s), 4.304.22 (3H, m), 4.02 (12H, dd, 3.5 Hz), 3.58 (2H, s), 2.77 (1H, dd, J=14.0, 6.8 Hz), 2.58 (1H, dd, J=14.0, 9.8 Hz), 2.33–2.21 (1H, m), 1.28 (3H, t, J=7.1 Hz).

C. Ethyl-1-(3-(4-phenyl-phenylmethyl)4-t-butyldimethylsilyloxy-chroman-7-yl)acetate To a solution of the trans-alcohol prepared in Example 3B (90 mg, 0.22 mmol) in DMF (1.0 mL) was added imidazole followed by t-butyidimethylsilyl chloride (335 µL, 1.0M solution in CH$_2$Cl$_2$, 0.335 mmol). After stirring at RT overnight, the solution was diluted with water and extracted with ether. The combined extracts were dried, filtered and concentrated. Flash chromatography, eluting with 6:1 hexane-ethyl acetate afforded 80 mg of a viscous, light yellow oil. $^1$HNMR (300 MHz, CDCl$_3$): 7.66–7.21 (9H, m), 7.23 (d, J=8.1 Hz), 6.87 (d, J=8.2 Hz), 6.82 (1H, s), 4.45 (1H, s), 4.32 (1H, dd, J=9.8, 2.1 Hz), 4.19 (2H, q, J=7.1 Hz), 4.06 (1H, d, J=9.8 Hz), 3.58 (2H, s), 2.57 (2H, d, J=8.3 Hz), 2.15–2.05 (1H, m), 1.30 (1H, t, J=7.0 Hz), 0.88 (9H, s), 0.07 (6H, s).

D. Ethyl-1-(3-(4-phenyl-phenylmethyl)-4-t-butyldimethylsiloxy-chroman-7-yl)-2-cyclopentene)-carboxylate To a solution of the ester prepared in Example 3C (70 mg, 0.13 mmol) in THF (4 mL) at about −78° C. was added potassium t-butoxide (150 µL, 1.0M solution in THF, 0.149 mmol) followed by DMPU (0.8 mL). The mixture was stirred for about 15 minutes at which time cis-1,4-dichloro-2-butene (19 mg, 0.149 mmol) was added. After about 1 hour, an additional amount of potassium t-butoxide was added and the resulting mixture was allowed to warm to RT and stirred overnight. The reaction was quenched with sat. aqueous ammonium chloride solution and extracted with methylene chloride. The combined extracts were washed with water, dried, filtered and evaporated. Flash chromatography, elution with 8:1 hexane-ethyl acetate provided 14 mg of the desired product. $^1$HNMR (300 MHz, CDCl$_3$): 7.62–7.18 (9H, m), 7.11 (1H, d, J=8.0 Hz), 6.91–6.82 (2H, m), 5.76 (2H, s), 4.45 (1H, s), 4.30 (1H, d, J=9.7 Hz), 4.25 (2H, q, J=7.0 Hz), 4.02 (1H, d, J=9.7 Hz), 3.40 (2H, d, J=14.2 Hz), 2.77 (2H, d, J=14.2 Hz), 2.77 (2H, d, J=14.2 Hz), 2.57 (2H, d, J=8.0 Hz), 1.20 (3H, t, J=7.0 Hz), 0.87 (9H, s), 0.07 (3H, s), 0.04 (3H, s).

E. 1-(3-(4-Phenyl-phenylmethyl)4-hydroxy-chroman-7-yl)-(2-cyclopentene)-carboxylic acid To a solution of the ester prepared in Example 3D in methanol (2.0 mL) was added 1N NaOH (1.0 mL) solution. The mixture was heated at about 60° C. for about 48 hrs at which time it was cooled and acidified with 1N solution. The mixture was extracted with methylene chloride and the combined extracts were dried, filtered and evaporated. Flash chromatography, eluting with 3:1 ethyl acetate-hexane with 1% acetic acid afforded 5 mg of the desired acid. $^1$HNMR (300 MHz, CDCl$_3$): 7.62–7.10 (10H, m), 6.98 (1H, d, J=9.0 Hz), 6.90 (1H, s), 5.77 (2H, s), 4.51 (1H, s), 4.23 (1H, dd, J=12.2, 3.0 Hz), 4.0 (1H, dd, J=12.1, 5.0 Hz), 3.40 (2H, s), 2.80–2.70 (3H, m), 2.57 (1H, dd, J=14.0, 9.2 Hz), 2.32–2.17 (1H, m).

EXAMPLES 5–9

The following compounds having the formula

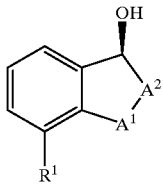

were synthesized using methods analogous to the indicated methods.

| Ex. No. | $R^1$ | $A^1$ | $A^2$ | | Prep. Method | Data |
|---|---|---|---|---|---|---|
| 5 | HNSO₂CF₃ (4-F phenyl) | O | | CH-CH₂-Ph | Ex.2, then Ex. 1I, J | M.P.: 108.1–110.3° C. |
| 6 | CO₂H (thiophene) | O | | CH-CH₂-Ph | Ex. 1 | M.P.: 154.6–155.9° C. $^{13}$CNMR (DMSO-$d_6$): 163.5, 153.7, 146.6, 140.0, 136.4, 132.0, 131.0, 129.9, 129.4 (2), 128.9 (2), 126.5, 125.0, 122.0, 117.1 66.3, 65.7, 41.9, 34.6. |
| 7 | CO₂H (furan) | O | | CH-CH₂-Ph | Ex. 1 | M.P.: 198.0–199.5° C. $^{13}$CNMR (DMSO-$d_6$): 164.8, 155.9, 154.0, 142.7, 139.9, 130.5, 130.2, 129.4 (2), 128.9 (2), 126.8, 126.6, 120.3, 115.9, 115.1, 113.8, 66.1, 65.9, 41.7, 34.6 |
| 8 | CO₂H (furan) | O | | CH-CH₂-Ph | Ex. 1 | M.P.: 167.8–168.9° C. $^{13}$CNMR (DMSO-$d_6$): 164.8, 155.9, 153.9, 142.7, 140.2, 130.8, 130.4, 129.5 (2), 128.8 (2), 127.2, 126.4, 119.9, 116.0, 115.0, 113.8, 65.2, 63.6, 40.2, 32.6. |
| 9 | HNSO₂CF₃ (4-F phenyl) | CH₂ | | CH-CH₂-Ph | * | HRMS: Calculated for $C_{24}H_{21}NO_3SF_4$: 479.1274. Found: 479.1197 |

*Using the compound of Preparation 1 and reacting it according to the methods described in Ex. 1I, J, yielded the instant compound.

PREPARATION 1

2-(6-Benzyl-5-hydroxy-5,6,7,8-tetrahydro-naphthalen-2-yl)-4-fluorobenzoic acid

A. 2-Benzylidene-6-methoxy-3,4-dihydro-2H-naphthalen-1-one

To a stirred solution of 6-methoxy-1-tetralone (227 mmole, 40 gm) and benzaldehyde (272 mmole, 27.5 mL) in 450 mL of methanol was added pyrrolidine (272 mmole, 23.6 mL). The mixture was stirred at room temperature for about 4 days until TLC indicated that no starting tetralone was present. The mixture was concentrated in vacuo, then dissolved in EtOAc, washed with four portions of 10% HCl, two portions of saturated NaHCO₃ solution, and one portion of brine. The solvent was removed in vacuo and the crude oil was triturated with diethyl ether to afford 38 g of the title compound of this Preparation 1A, mp 100–102° C. Analysis calculated for $C_{18}H_{16}O_2$: 264.1146. Found: 264.1149.

B. 2-Benzyl-6-methoxy-3,4-dihydro-2H-naphthalen-1-one

A Parr® hydrogenation bottle was charged with naphthalen-1-one (15 gm), ethyl acetate (150 mL) and 1 g of 10% palladium on charcoal. The mixture was hydrogenated on a Parr® shaker for about 15 hrs under 20 psi of hydrogen. The resulting mixture was filtered through a pad of Celite® and concentrated in vacuo to afford a red oil which was purified by flash chromatography (3:1 hexane/diethyl ether) to afford 14.1 gm of benzyltetralone, mp 50–51° C. Analysis calculated for $C_{18}H_{18}O_2$: 266.1302. Found: 266.1308.

C. 2-Benzyl-6-hydroxy-3,4-dihydro-2H-naphthalen-1-one

To a stirred solution of benzyltetralone (5 gm, 19 mmole) in methylene chloride (40 mL) at about −78° C. was added boron tribromide (1.95 mL, 21 mmole). The cooling bath was removed and the reaction mixture was stirred overnight at room temperature, after which time an additional 1.5 mL of boron tribromide was added. Stirring was continued at room temperature for about another 4 hrs at which time the mixture was poured into ice water and stirred for about 0.5 hr. The aqueous mixture was saturated with sodium chloride and extracted with four portions of methylene chloride. The layers were separated and the organic phase was washed with water and dried over anhydrous sodium sulfate. Filtration and removal of the solvent in vacuo afforded a brown solid which was purified by flash chromatography (3:2 hexane/ether) to afford 3 gm of the phenol, mp 160–162° C. Analysis calculated for $C_{17}H_{16}O_2$: 252.1146. Found: 252.1144.

D. Trifluoromethanesulfonic acid 6-benzyl-5-oxo-5,6,7,8-tetrahydro-naphthalen-2-yl ester To a stirred solution of the phenol (2.75 gm, 11 mmole), triethylamine (4.56 mL, 33 mmole) and DMAP (0.05 gm) in methylene chloride (100 mL) at about −78° C. was added trifluoromethanesulfonic anhydride (2 mL, 12 mmole). The cooling bath was removed and the reaction mixture was warmed to room temperature and stirred overnight. The mixture was then poured into ice water and extracted with ethyl acetate. The resulting organic layer was washed with water, dried over anhydrous sodium sulfate, filtered and the solvent was removed in vacuo. The crude product was purified by flash chromatography to afford 3.9 gm of triflate, mp 52–53.7° C. Analysis calculated for $C_{18}H_{15}O_4SF_3$: 384.0638. Found: 384.0602.

E. 2-Benzyl-6-[2-(4,4-dimethyl-4,5-dihydro-oxazol-2-yl)-5-fluorophenyl]-3,4-dihydro-2H-naphthalen-1-one To a stirred solution of n-butyllithium (3.6 mL of a 2.5M solution in hexanes, 9 mmole) in toluene (10 mL) at about −40° C. was added a solution of aryl oxazoline (1.76 gm, 9 mmole) in toluene (5 mL) dropwise via cannula. The mixture was stirred at about −40° C. for about 0.5 hr then warmed to about −25° C. and stirred for about another 1 hr. To this mixture was added zinc chloride (9 mL of a 1M solution in diethyl ether, 9 mmole). The cooling bath was removed and the mixture was warmed to room temperature and stirred for about 1 hr. The resulting mixture was added via cannula to a solution of tetralone triflate (3.5 gm, 9 mmole) and palladium tetrakistriphenylphosphine (0.5 mmole, 0.63 gm) in tetrahydrofuran (15 mL). The reaction mixture was heated to reflux for about 2 hr, cooled to room temperature and poured into saturated aqueous ammonium chloride solution. The aqueous mixture was extracted with three portions of ethyl acetate. The organic phase was washed with three portions of 1M HCl, saturated aqueous sodium bicarbonate and brine. The organic phase was then dried over anhydrous sodium sulfate, filtered an the solvent was removed in vacuo. The crude product was purified by flash chromatography (2:1 diethyl ether/hexane) to afford 2.07 gm of the coupled product, mp 114–115° C. Analysis calculated for $C_{28}H_{26}NO_2F$: 427.1948. Found: 427.1956.

F. 2-Benzyl-6-[2-(4,4-dimethyl-4,5-dihydro-oxazol-2-yl)-5-fluorophenyl]-1,2,3,4-tetrahydro-naphthalen-1-ol To a stirred solution of tetralone oxazoline (1.5 gm, 3.5 mmol) in methanol (35 mL) was added sodium borohydride (0.20 gm, 5.25 mmole). The resulting brown mixture was stirred at room temperature for about 1 hr, then poured into brine and extracted with three portions of ethyl acetate. The organic phase was dried over anhydrous sodium sulfate and the solvent removed in vacuo to afford 1.20 gm of a 1:1 mixture of cis and trans alcohols, mp 88–89° C. Analysis calculated for $C_{28}H_2BNO_2F$: 429.2087. Found: 429.2067.

G. 2-(6Benzyl-5-hydroxy-5,6,7,8-tetrahydro-naphthalen-2-yl)-4-fluorobenzoic acid The oxazoline (1.0 gm, 2.34 mmol) was dissolved in 5 mL of methyl iodide and stirred at room temperature for about 2 days, at which time the methyl iodide was removed in vacuo. The residue was taken up in methylene chloride and concentrated in order to remove traces of residual methyl iodide. The dark red residue was dissolved in methanol (5 mL) and 2N NaOH (5 mL) was added. The resulting mixture was heated to reflux with stirring for about 5 hrs. The mixture was then cooled to room temperature and acidified with 3N HCl. The resulting slurry was extracted with three portions of ethyl acetate and the combined organic phase was washed with brine. The organic phase was dried over anhydrous sodium sulfate and the solvent removed in vacuo to afford 0.80 gm of the carboxylic acid alcohol. $^1$HNMR (250 MHz., methanol-d$_4$) δ: 7.83 (dd, 1H, J=7.0, 7.5), 7.50 (d, 1H, J=7.0), 7.30–7.00 (m, 9H×2), 4.50 (d,1H, J=2.0), 4.41 (d, 1H, J=8.0), 3.15 (dd, 1H, J=5.4, 13.9), 3.00–2.57 (m, 4H), 2.42 (dd, 1H, J=11.4, 13.5), 2.09–1.35 (m, 5H×2).

What is claimed is:

1. A compound of the formula

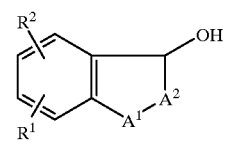

(I)

and the pharmaceutically acceptable salts thereof wherein $A^1$ is NH or N(C$_1$–C$_6$)alkyl;

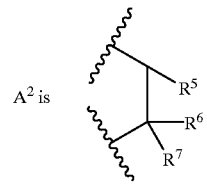

$R^5$ is selected from the group consisting of —(CH$_2$)$_n$X$^{10}$, wherein n is 0, 1, 2, or 3;

X$^{10}$ is one of the following optionally substituted rings: phenyl, thienyl, pyridyl, furyl, naphthyl, quinolyl, isoquinolyl, pyrimidinyl or pyrazinyl;

where the optionally substituted rings are optionally substituted with one or two substituents independently selected from the group consisting of fluoro, chloro, (C$_1$–C$_6$)alkyl, (C$_1$–C$_6$)alkoxy, (C$_1$–C$_4$)perfluoroalkyl, (C$_1$–C$_4$)perfluoroalkoxy, and optionally substituted phenyl;

where the optionally substituted phenyl is optionally substituted with one or two substituents independently selected from the group consisting of fluoro, chloro, (C$_1$–C$_6$)alkyl, (C$_1$–C$_6$)alkoxy, (C$_1$–C$_4$)perfluoroalkyl, (C$_1$–C$_4$)perfluoroalkoxy;

$R^6$ and Re are each independently hydrogen or (C$_1$–C$_4$) alkyl or $R^6$ and $R^7$ are taken together with the carbon atom to which they are attached and form (C$_4$–C$_7$) cycloalkyl:

R$^1$ is a substituted phenyl or five or six membered heteroaromatic ring containing one or two heteroatoms where the heteroatoms are independently selected from the group consisting of O, S and N; the substituted phenyl ring is substituted with one substituent selected from the group consisting of, —N(H)(SO$_2$—X$^7$), —N(H)(CO—X$^7$). and —N(H)(CO—O lower alkyl) and with one or two substituents each independently selected from the group consisting of fluoro, chloro, (C$_1$–C$_6$)alkyl, (C$_1$–C$_6$)alkoxy, (C$_1$–C$_4$)perfluoroalkyl, (C$_1$–C$_4$)perfluoroalkoxy, and the substituted five or six membered hetero aromatic ring is substituted with one substituent selected from the group consisting of carboxy, tetrazolyl,—CO—N(H)(SO$_2$—X$^7$), —N(H)(SO$_2$—X$^7$), —N(H)(CO—X$^7$), and —N(H)(CO—O lower alkyl) and with one or two substituents each independently selected from the group consisting of fluoro, chloro, (C$_1$–C$_6$)alkyl, (C$_1$–C$_6$)alkoxy, (C$_1$–C$_4$) perfluoroalkyl, (C$_1$–C$_4$)perfluoroalkoxy.

wherein X$^7$ is —CF$_3$, (C$_1$–C$_6$)alkyl, (C$_3$–C$_8$)cycloalkyl or one of the following optionally substituted rings: phenyl, thienyl, pyridyl, furyl, naphthyl, quinolyl, isoquinolyl, pyrimidinyl or pyrazinyl;

where the optionally substituted rings are optionally substituted with one or two substituents independently selected from the group consisting of fluoro, chloro, (C$_1$–C$_6$)alkyl, (C$_1$–C$_6$)alkoxy, (C$_1$–C$_4$)perfluoroalkyl, (C$_1$–C$_4$)perfluoroalkoxy, and optionally substituted phenyl;

where the optionally substituted phenyl is optionally substituted with one or two substituents independently selected from the group consisting of fluoro, chloro, (C$_1$–C$_6$)alkyl, (C$_1$–C$_6$)alkoxy, (C$_1$–C$_4$)perfluoroalkyl, (C$_1$–C$_4$)perfluoroalkoxy;

and R$^2$ is hydrogen, fluoro, chloro, (C$_1$–C$_6$)alkyl, (C$_1$–C$_6$) alkoxy, (C$_1$–C$_4$)perfluoroalkyl, (C$_1$–C$_4$) perfluoroalkoxy, (C$_1$–C$_6$)alkylthio, (C$_1$–C$_6$) alkylsulfinyl, phenylsulfinyl, (C$_1$–C$_6$)alkylsulfonyl or phenylsulfonyl.

2. A compound according to claim 1 or a pharmaceutically acceptable salt thereof wherein A$^2$ is

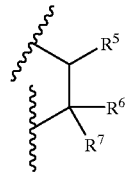

wherein R$^6$ and R$^7$ are each hydrogen.

3. A compound according to claim 2 or a pharmaceutically acceptable salt thereof wherein R$^1$ is a substituted phenyl substituted with one substitutuents selected from the group consisting of —N(H)(SO$_2$—X$^7$), —N(H)(O—O-lower alkyl) and with one or two substituents each independently selected from the group consisting of fluoro, chloro, (C$_1$–C$_6$) alkyl, (C$_1$–C$_6$)alkoxy, (C$_1$–C$_4$)perfluoroalkyl, and (C$_1$–C$_4$) perfluoroalkoxy or a substituted five or six membered hetero aromatic ring substituted with one substituent selected from the group consisting of carboxy, tetrazolyl, —CO—N(H) (SO$_2$—X$^7$), —N(H)(SO$_2$—X$^7$), —N(H)(CO—X$^7$), and —N(H)(CO—O lower alkyl) and with one or two substituents each independently selected from the group consisting of fluoro, chloro, (C$_1$–C$_6$)alkyl, (C$_1$–C$_6$)alkoxy, (C$_1$–C$_4$) perfluoroalkyl, and (C$_1$–C$_4$)perfluoroalkoxy.

4. A compound according to claim 3 or a pharmaceutically acceptable salt thereof wherein R$^1$ is a substituted phenyl substituted with one substituent selected from the group consisting of, —N(H)(SO$_2$—X$^7$), —N(H)(CO—X$^7$), and —N(H)(CO—O lower alkyl) and with one or two substituents each independently selected from the group consisting of fluoro, chloro, (C$_1$–C$_6$)alkyl, (C$_1$–C$_6$)alkoxy, (C$_1$–C$_4$) perfluoroalkyl, and (C$_1$–C$_4$)perfluoroalkoxy.

5. A compound according to claim 4 or a pharmaceutically acceptable salt thereof wherein R$^1$ is a substituted phenyl substituted with —N(H)(SO$_2$—X$^7$), and with one or two substituents each independently selected from the group consisting of fluoro, chloro, (C$_1$–C$_6$)alkyl, (C$_1$–C$_6$)alkoxy, (C$_1$–C$_4$)perfluoroalkyl, and (C$_1$–C$_4$)perfluoroalkoxy.

6. A compound according to claim 5 or a pharmaceutically acceptable salt thereof wherein n is 1; and X$^{10}$ is phenyl or phenyl substituted at the para position with phenyl.

7. A compound according to claim 6 or a pharmaceutically acceptable salt thereof wherein R$^1$ is a substituted phenyl substituted with —N(H)(SO$_2$—X$^7$), and with one or two substituents each independently selected from the group consisting of fluoro, chloro and (C$_1$–C$_4$)perfluoroalkyl.

8. A pharmaceutical composition for the treatment of LTB$_4$ induced illnesses which comprises an effective amount of a compound according to claim 1 or a pharmaceutically acceptable salt thereof and a pharmaceutically acceptable carrier or diluent.

9. A pharmaceutical composition for the treatment of anti-inflammatory disorders, eczema, erythema, pruritus, acne, stroke, graft rejection, autoimmune diseases, and asthma, which comprises an effective amount of a compound according to claim 1 or a pharmaceutically acceptable salt thereof and a pharmaceutically acceptable carrier or diluent.

10. A method for receptor binding inhibition, functional inhibition and in vivo inhibition of LTB$_4$ which comprises administering to a subject in need of such inhibition a compound according to claim 1 or a pharmaceutically acceptable salt thereof.

11. A method for the treatment of inflammatory disorders, eczema, erythema, pruritus, acne, stroke, graft rejection, autoimmune diseases, and asthma, which comprises administering to a subject in need of such treatment a compound according to claim 1 or a pharmaceutically acceptable salt thereof.

12. A compound of the formula

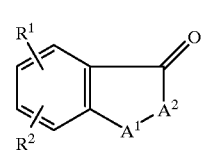

(I)

wherein A$^1$ is NH or N(C$_1$–C$_6$)alkyl;

A$^2$ is 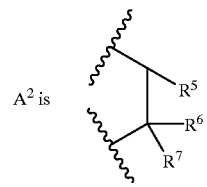

R$^5$ is selected from the group consisting of —(CH$_2$)$_n$X$^{10}$, wherein n is 0, 1, 2, or 3;

$X^{10}$ is one of the following optionally substituted rings: phenyl, thienyl, pyridyl, furyl, naphthyl quinolyl, isoquinolyl, pyrimidinyl or pyrazinyl;

where the optionally substituted rings are optionally substituted with fluoro, chloro, $(C_1-C_6)$alkyl, $(C_1-C_6)$ alkoxy, $(C_1-C_4)$perfluoro-alkyl, $(C_1-C_4)$ perfluoroalkoxy and optionally substituted phenyl;

where the optionally substituted phenyl is optionally substituted with one or two substituents independently selected from the group consisting of fluoro, chloro, $(C_1-C_6)$alkyl, $(C_1-C_6)$alkoxy, $(C_1-C_4)$perfluoroalkyl, and $(C_1-C_4)$perfluoroalkoxy, $R^6$ and $R^7$ are each independently hydrogen or $(C_1-C_4)$ alkyl, or $R^6$ and $R^7$ are taken together with the carbon atom to which they are attached and form $(C_4-C_7)$ cycloalkyl;

$R^1$ is a substituted phenyl or a 5 or 6 membered heteraromatic ring optionally having one or two heteroatoms where the heteroatoms are independently selected from the group consisting of O, S and N;

the substituted phenyl ring is substituted with one 'substituent selected from the group consisting of —N(H)(SO$_2$-X$^7$), —N(H)(CO—X$^7$), and —N(H)(CO—O lower alkyl) and with one or two substituents each independently selected from the group consisting of fluoro, chloro, $(C_1-C_6)$alkyl, $(C_1-C_6)$alkoxy, $(C_1-C_4)$ perfluoroalkyl, $(C_1-C_4)$perfluoroalkoxy and substituted five or six membered hetero aromatic ring is substituted with one substituent selected from the group consisting of carboxy, tetrazolyl, —CO—N(H)(SO$_2$—X$^7$), —N(H)(SO$_2$—X$^7$), —N(H)(CO—X$^7$), and —N(H)(CO—O lower alkyl) and with one or two substituents each independently selected from the group consisting of fluoro, chloro, $(C_1-C_6)$alkyl, $(C_1-C_6)$alkoxy, $(C_1-C_4)$perfluoroalkyl, $(C_1-C_4)$perfluoroalkoxy, wherein $X^7$ is —CF$_3$, $(C_1-C_6)$alkyl, $(C_3-C_8)$cyclo-alkyl or one of the following optionally substituted rings: phenyl, thienyl, pyridyl, furyl, naphthyl, quinolyl, isoquinolyl, pyrimidinyl or pyrazinyl;

where the optionally substituted rings are optionally substituted with one or two substituents independently selected from fluoro, chloro, $(C_1-C_6)$alkyl, $(C_1-C_6)$ alkoxy. $(C_1-C_4)$perfluoroalkyl. $(C_1-C_4)$ perfluoroalkoxy, and optionally substituted phenyl; where the optionally substituted phenyl is optionally substituted with one or two substituents independently selected from the group consisting of fluoro, chloro, $(C_1-C_6)$alkyl, $(C_1-C_6)$alkoxy, $(C_1-C_4)$perfluoroalkyl, $(C_1C_4)$perfluoroalkoxy;

$R^2$ is hydrogen, fluoro, chloro, $(C_1-C_6)$alkyl, $(C_1-C_6)$ alkoxy, $(C_1-C_4)$perfluoroalkyl, $(C_1-C_4)$ perfluoroalkoxy, $(C_1-C_6)$alkylthio, $(C_1-C_6)$ alkylsulfinyl, phenylsulfinyl, $(C_1-C_6)$alkylsulfonyl or phenylsulfonyl.

* * * * *